(12) United States Patent
Ogo et al.

(10) Patent No.: US 8,722,376 B2
(45) Date of Patent: May 13, 2014

(54) FIREFLY LUCIFERASE

(75) Inventors: Katsunori Ogo, Hachioji (JP); Ryutaro Akiyoshi, Hachioji (JP); Hirobumi Suzuki, Hino (JP)

(73) Assignees: Olympus Corporation, Tokyo (JP); Nimura Genetic Solutions Co., Ltd., Tokyo (JP); Perak State Development Corporation, Perak Darul Ridzuan (MY)

( * ) Notice: Subject to any disclaimer, the term of this patent is extended or adjusted under 35 U.S.C. 154(b) by 0 days.

(21) Appl. No.: 13/589,453

(22) Filed: Aug. 20, 2012

(65) Prior Publication Data
US 2013/0040326 A1  Feb. 14, 2013

Related U.S. Application Data

(63) Continuation of application No. PCT/JP2011/054841, filed on Feb. 24, 2011.

(51) Int. Cl.
C12N 9/02 (2006.01)
C12N 15/53 (2006.01)

(52) U.S. Cl.
USPC ........................................................ 435/189

(58) Field of Classification Search
None
See application file for complete search history.

(56) References Cited

FOREIGN PATENT DOCUMENTS

JP    2006-301599    11/2006
WO   WO 2006/088109 A1   8/2006

OTHER PUBLICATIONS

Hou Q.B., Li X.Y., Ohmiya Y., Liang X.C. "Molecular cloning, expression and sequence analysis of luciferase RT from *Luciola terminalis*." Submitted (Nov. 2007) to the EMBL/GenBank/DDBJ databases UniProtID B3TMS5_9COLE.*
Kim J., Choi Y., Jin B. "Genomic Structure of the Luciferase Gene in the *Luciola lateralis*." Submitted (Dec. 2002) to the EMBL/GenBank/DDBJ databases UniProtID Q27348_LUCLA.*
Isobe, Minoru et al., "Chemistry of photoproteins as interface between bioactive molecules and protein function", Pure & Appl, Chemistry (Jan. 1, 1998), vol. 70, No. 11, pp. 2085-2092.
Kim, Jong Gill et al., "Genomic Structure and phylogenetic analysis of the luciferase gene of the firefly, *Luciola lateralis* (Coleoptera: Lampyridae)", European Journal of Entomology (2004), vol. 101, No. 1, pp. 1-11.
International Search Report dated Jul. 29, 2011 issued in PCT/JP2011/054841.

* cited by examiner

*Primary Examiner* — Lisa J Hobbs
(74) *Attorney, Agent, or Firm* — Scully, Scott, Murphy & Presser, P.C.

(57) ABSTRACT

According to one embodiment, the present invention relates to luciferase derived from Malaysian *Luciola* firefly, the luciferase having a maximum luminescent wavelength of 580 nm at pH 8, or the luciferase indicating 23.3 times or more of luminescent intensity in comparison to that of Rhodamine 6G.

4 Claims, 5 Drawing Sheets

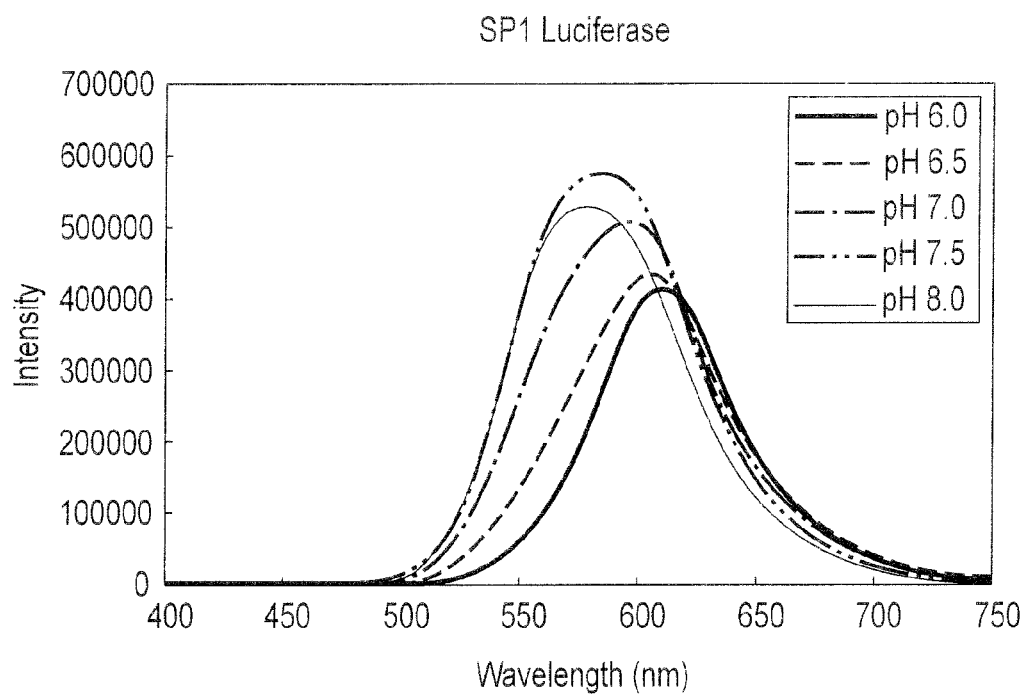
F I G. 1
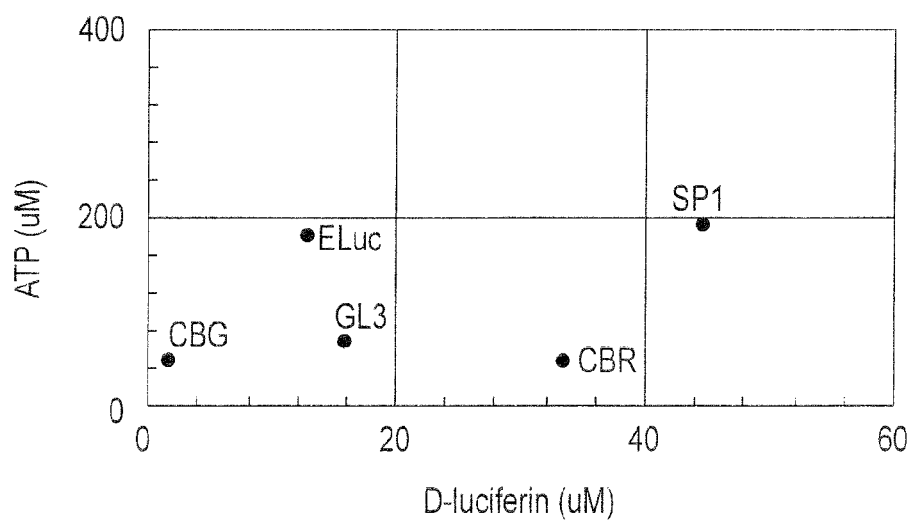
F I G. 2

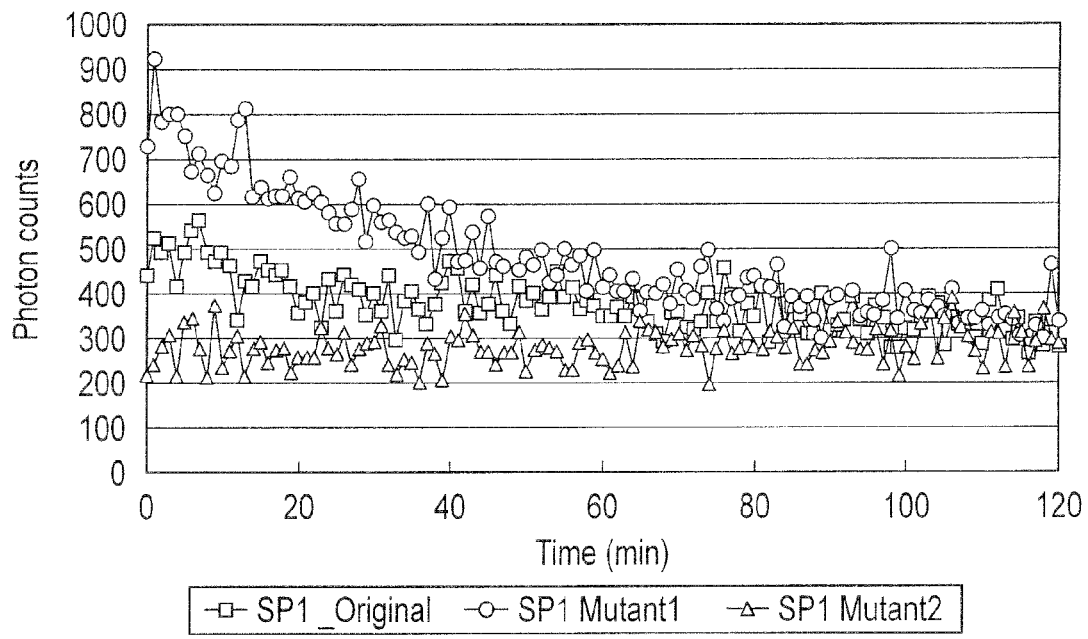
F I G. 5
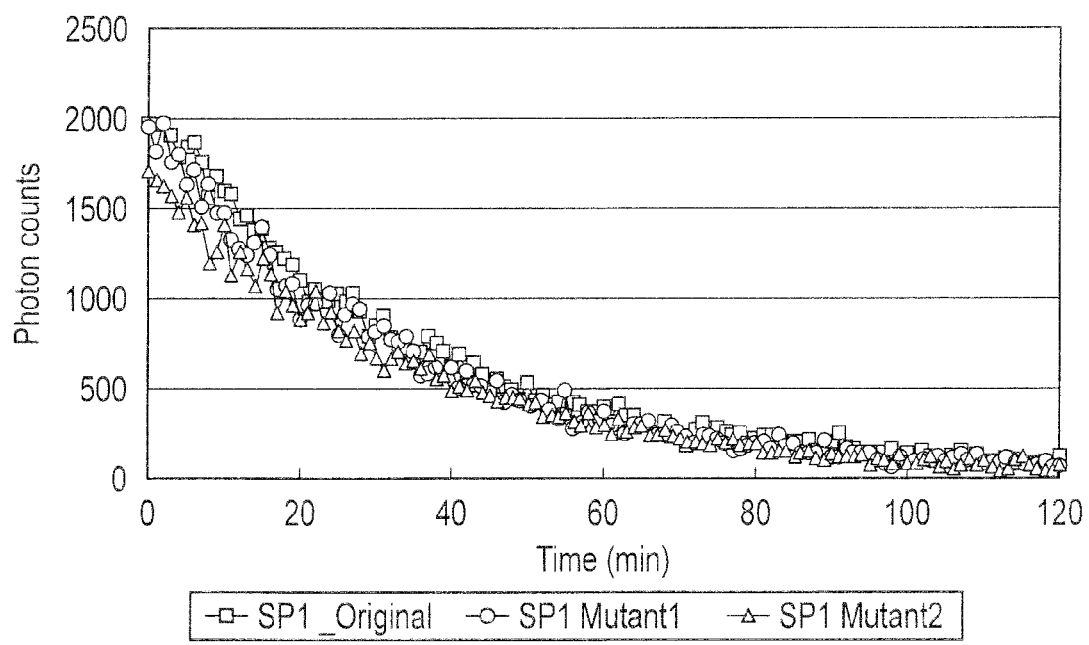
F I G. 6

SEQUENCE LISTING

<160> NUMBER OF SEQ ID NOS: 38

<210> SEQ ID NO 1
<211> LENGTH: 548
<212> TYPE: PRT
<213> ORGANISM: Luciola sp.

<400> SEQUENCE: 1

Met Asn Asn Met Asp Asp Gly Glu His Ile Val Val Gly Pro Gln Pro
1               5                   10                  15

Phe Tyr Pro Val Glu Glu Gly Ser Ala Gly Thr Gln Leu Leu Lys Tyr
            20                  25                  30

Leu Lys Gln Tyr Ser Lys Leu Gly Ala Ile Ala Phe Ser Asn Ala His
        35                  40                  45

Thr Lys Val Asp Ile Ser Tyr Ala Glu Tyr Leu Asp Thr Ser Val Arg
    50                  55                  60

Leu Ala Gln Ala Leu Ile Asn Tyr Gly Ile Pro Ile Asp Gly Arg Ile
65                  70                  75                  80

Ala Leu Cys Ser Glu Asn Cys Glu Glu Phe Tyr Phe Pro Val Leu Ala
                85                  90                  95

Gly Leu Tyr Ile Gly Ala Gly Val Ala Pro Thr Asn Glu Ile Tyr Thr
            100                 105                 110

Leu Arg Glu Leu Val His Ser Leu Gly Ile Ser Lys Pro Thr Ile Val
        115                 120                 125

Phe Ser Ser Lys Lys Gly Leu Glu Lys Val Ile Thr Val Gln Lys Thr
    130                 135                 140

Val Thr Cys Ile Lys Thr Ile Val Ile Leu Asp Ser Lys Val Asp Tyr
145                 150                 155                 160

Gln Gly Tyr Asp Cys Leu Glu Thr Phe Ile Lys Lys Tyr Leu Pro Ala
                165                 170                 175

Gly Phe Ser Val Glu Asn Phe Ile Pro Arg Glu Val Asn Arg Lys Glu
            180                 185                 190

Gln Val Ala Leu Val Met Asn Ser Ser Gly Ser Thr Gly Leu Pro Lys
        195                 200                 205

Gly Val Gln Ile Thr His Glu Gly Ala Val Thr Arg Phe Ser His Ala
    210                 215                 220

Arg Asp Pro Ile Tyr Gly Asn Gln Val Ser Pro Gly Thr Ala Ile Leu
225                 230                 235                 240

Thr Ile Val Pro Phe His His Gly Phe Gly Met Phe Thr Asn Leu Gly
                245                 250                 255

Tyr Leu Thr Cys Gly Tyr Arg Ile Val Met Leu Thr Lys Phe Asp Glu
            260                 265                 270

Glu Leu Phe Leu Lys Thr Leu Ala Asp Tyr Lys Cys Thr Ser Val Ile
            275                 280                 285

Leu Val Pro Thr Leu Phe Ala Ile Leu Ser Lys Ser Val Leu Leu Glu
            290                 295                 300

Lys Tyr Asp Leu Ser Asn Leu Val Glu Ile Ala Ser Gly Gly Ala Pro
305                 310                 315                 320

Leu Ala Lys Glu Val Gly Glu Ala Val Ala Arg Arg Phe Asn Leu Pro
            325                 330                 335

Gly Ile Arg Gln Gly Tyr Gly Leu Thr Glu Thr Thr Ser Ala Ile Ile
            340                 345                 350

Ile Thr Pro Glu Gly Asp Asp Lys Pro Gly Ala Ser Gly Lys Ile Val
            355                 360                 365

Pro Leu Phe Arg Ala Lys Val Val Asp Leu Asp Thr Gln Lys Thr Leu
            370                 375                 380

Gly Pro Asn Arg Arg Gly Glu Ile Cys Val Lys Gly Pro Met Leu Met
385                 390                 395                 400

Lys Gly Tyr Val Asp Asp Pro Val Ala Thr Ser Gln Ile Ile Asp Lys
            405                 410                 415

Asp Gly Trp Leu His Thr Gly Asp Ile Gly Tyr Phe Asp Glu Asp Lys
            420                 425                 430

His Phe Phe Ile Val Asp Arg Leu Lys Ser Leu Ile Lys Tyr Lys Gly
            435                 440                 445

Tyr Gln Val Pro Pro Ala Glu Leu Glu Ser Val Leu Leu Gln His Pro
            450                 455                 460

Asp Ile Phe Asp Ala Gly Val Ala Gly Leu Pro Asp Pro Leu Ala Gly
465                 470                 475                 480

Glu Leu Pro Gly Ala Val Val Val Leu Glu Lys Gly Arg His Met Thr
            485                 490                 495

Glu Gln Gln Val Met Asp Tyr Val Ala Gly Gln Val Ser Asn Ala Lys
            500                 505                 510

Arg Leu Arg Gly Gly Val Arg Phe Val Asp Glu Val Pro Lys Gly Leu
            515                 520                 525

Thr Gly Lys Ile Asp Ser Lys Ala Ile Arg Glu Ile Leu Lys Ser Pro
            530                 535                 540

Lys Ala Lys Met
545

<210> SEQ ID NO 2
<211> LENGTH: 1647
<212> TYPE: DNA
<213> ORGANISM: Luciola sp.

<400> SEQUENCE: 2
atgaataaca tggatgacgg agaacatatt gtagttggtc cccaacccttt ttaccctgta      60 gaagagggta gcgcaggaac acagttgcta aaatacctta agcaatattc aaaacttggt     120
gccattgctt ttagcaacgc ccatactaaa gttgatattt catatgcaga atacttagac     180
acatcagtcc gtttagctca ggctttgatc aattatggta ttccgataga cggaagaatc     240
gcgttgtgca gtgaaaattg cgaggaattc tatttcccag tacttgctgg acttacata      300 ggcgcaggtg ttgctcctac taatgaaatt tacaccttac gtgaattggt tcatagctta     360
ggtatctcaa aaccaacaat tgtattcagc tcgaagaaag gtttagaaaa agttataacg     420

```
gtacagaaaa cggtaacttg cattaaaaca attgtcatat tagacagcaa agtcgattat    480
caaggatatg attgtctgga gaccttcatt aaaaaatatt taccagcagg attttcagtt    540
gaaaatttta tacctcggga ggttaaccgt aaagaacagg ttgctctcgt aatgaactct    600
tcgggttcca ccggtttacc aaaaggtgta caaatcaccc atgaaggcgc agttactaga    660
ttttcccacg ccagggatcc aatttatgga aatcaagtgt cacctggtac agctatctta    720
actattgttc catttcatca tggttttgga atgttcacca atttgggata cttaacttgt    780
ggctatcgta ttgttatgtt aacaaaattc gatgaagaat tgttttttgaa aactttggcc    840 gactacaaat gtacaagcgt gatccttgtt ccgactttat ttgcaattct ctcaaaaagt    900
gttctacttg aaaaatacga tctttcaaat ctggttgaaa ttgcatctgg tggagctccg    960
ttagccaaag aagtaggcga agcggttgct agacggttta atctaccggg tattcgtcaa   1020
ggttacggtt taaccgaaac aacatctgcc attatcatca caccagaagg tgacgataag   1080
ccaggtgcat ctggaaaaat tgttccactt tttagagcaa aagttgttga tcttgacact   1140
caaaagactt taggtcccaa tagacgagga gaaatatgcg taaagggacc tatgctcatg   1200
aaaggttacg tagatgatcc agtagctaca agtcaaatta ttgacaaaga tggttggttg   1260
cacacaggag atattggata tttcgacgaa gacaaacatt tcttcattgt tgatcgttta   1320
aaatctttaa taaaatacaa aggataccaa gtaccacctg ccgaattgga atctgtgctt   1380
ttgcaacatc ccgatatctt tgatgctggt gtggctggtt tacctgaccc gttagccggt   1440
gaacttccag gggcagttgt tgtacttgaa aaaggaagac atatgactga acagcaagtt   1500
atggattacg ttgcaggtca agtttcaaac gcaaaacgct taagaggtgg tgtccgcttt   1560
gtggatgaag tacctaaagg tcttactgga aaaattgaca gcaaagcaat tagagaaatt   1620
cttaaatcgc cgaaagccaa aatgtag                                       1647

<210> SEQ ID NO 3
<211> LENGTH: 1647
<212> TYPE: DNA
<213> ORGANISM: Luciola sp.

<400> SEQUENCE: 3
atgaataaca tggatgacgg agaacatatt gtagttggtc cccaaccttt ttaccctgta     60
gaagagggta gcgcaggaac acagttgcta aaataccta agcaatattc aaaacttggt    120
gccattgctt ttagcaacgc ccatactaaa gttgatattt catatgcaga atacttagac    180
acatcagtcc gtttagctca ggctttgatc aattatggta ttccgataga cggaagaatc    240
gcgttgtgca gtgaaaattg cgaggagttc tatttcccag tacttgctgg actttacata    300
ggcgcaggtt ttgctcctac taatgaaatt tacaccttac gtgaattggt tcatagctta    360
ggtatctcaa aaccaacaat tgtattcagc tcgaagaaag gtttagaaaa agttataacg    420
gtacagaaaa cggtaacttg cattaaaaca attgtcatat tagacagcaa agtcgattat    480
caaggatatg attgtctgga gaccttcatt aaaaaatatt taccagcagg attttcagtt    540
gaaaatttta tacctcggga ggttaaccgt aaagaacagg ttgctctcgt aatgaactct    600
tcgggttcca ccggtttacc aaaaggtgta caaatcaccc atgaaggcgc agttactaga    660
ttttcccacg ccagggaccc aatttatgga aatcaagtgt cacctggtac agctatctta    720
actattgttc catttcatca tggttttgga atgttcacca atttgggata cttaacttgt    780
ggctatcgta ttgttatgtt aacaaaattc gatgaagaat tgttttttgaa aaccttggcc    840 gactacaaat gtacaagcgt gatccttgtt ccgactttat ttgcaattct ctcaaaaagt    900
```

-continued

```
gttctacttg aaaaatacga tctttcaaat ctggttgaaa ttgcatctgg tggagctccg    960
ttagccaaag aagtaggcga agcggttgct agacggttta atctaccggg tattcgtcaa   1020
ggttacggtt taaccgaaac aacatctgcc attatcatca caccagaagg agacgataag   1080
ccaggtgcat ctggaaaaat tgttccactt tttagagcaa aagttgttga tcttgacact   1140
caaaagactt taggtcccaa tagacgagga gaaatatgcg taaagggacc tatgctcatg   1200
aaaggttacg tagatgatcc agtagctaca agtcaaatta ttgacaaaga tggttggttg   1260
cacacaggag atattggata tttcgacgaa gacaaacatt tcttcattgt tgatcgttta   1320
aaatctttaa taaaatacaa aggataccaa gtaccacctg ccgaattgga atctgtgctt   1380
ttacaacatc ccgatatctt tgatgctggt gtggctggtt acctgacccc gttagccggt   1440
gaacttccag gggcagttgt tgtacttgaa aaaggaagac atatgactga acagcaagtt   1500
atggattacg ttgcaggtca agtttcaaac gcaaacgcc taagaggtgg tgtccgcttt   1560
gtggatgaag tacctaaagg tcttactgga aaaattgaca gcaaagcaat tagagaaatt   1620
cttaaatcgc cgaaagccaa aatgtag                                       1647
```

```
<210> SEQ ID NO 4
<211> LENGTH: 1647
<212> TYPE: DNA
<213> ORGANISM: Luciola sp.

<400> SEQUENCE: 4
```

```
atgaataata tggatgacgg tgaacacatc gtggttgggc ctcaaccatt ttacccggtt     60
gaagaagggt ccgctggcac gcagctgctc aagtacctga agcaatattc caaacttgga    120
gcgattgcct tttccaatgc tcatactaag gtggacatca gctatgcaga gtacttggac    180
accagcgttc ggttggctca ggccctgatc aactacggaa tccctattga tgggcggata    240
gccctgtgct cagagaactg tgaggagttt tattttccag tcctcgctgg attgtacatt    300
ggtgctgggg tggctccaac taacgaaatc tacacactca gggagctggt gcactctctg    360
gggataagta aacccactat tgtgttctcc tccaaaaagg gactggagaa ggttatcacc    420
gttcaaaaga cagtgacctg catcaaaacc atcgtgatcc tcgatagcaa ggtcgattat    480
caaggttacg actgcttgga aacctttata aaaaatacc tgcctgccgg attcagcgtg    540
gagaacttta ttccgagaga ggtaaacagg aagaacagg tcgcactggt catgaacagc    600
tcaggtagca ctgggctgcc gaaaggcgtc caaattactc atgagggcgc ggtcacgaga    660
ttctcacatg ctcgcgatcc tatctatggc aaccaggttt caccaggcac cgctattctg    720
acaattgtcc cattccatca cggctttggg atgtttacca acctgggcta tctgacctgc    780
ggataccgca tcgtcatgtt gacaaagttc gatgaagaac tgtttctcaa aacgctggcc    840
gattataagt gtacttctgt gatcctggtg ccaaccctgt ttgccattct tagcaaatcc    900
gtgttgctgg agaagtatga ccttttccaac cttgttgaaa tcgccagcgg tggggcccct    960
ctggccaagg aagttggcga ggccgtggca cgaaggttta acctgccagg gattcgccag   1020
gggtatgggc tgaccgaaac aacaagtgcc ataatcatta ctcccgaagg ggacgataaa   1080
cccggagcct caggaaagat cgtgcctctg ttcagagcga aggtggttga tctggacact   1140
cagaagactc ttgacctaa tagaaggggc gagatctgcg tgaaaggacc catgttgatg   1200
aagggctatg tcgatgatcc agtcgccaca agtcaaatta tcgacaagga cggctggctg   1260
catacagggg atataggata tttcgatgag gataagcact tcttcatcgt cgaccgactc   1320
aagtccctga ttaaatacaa gggataccag gtcccacctg cggaactcga aagcgtcctc   1380
```

-continued

```
ctccagcatc cggacatctt tgatgcaggt gtggccgggc ttccagatcc attggcaggc   1440
gaactcccag gtgccgtcgt tgttttggag aaaggccgac acatgaccga acagcaggtc   1500
atggactacg tcgcaggtca agtcagcaat gcgaagaggc ttcgaggcgg cgtgagattc   1560
gtggatgagg tgccgaaggg actgaccggc aagatcgaca gtaaggccat acgcgaaatc   1620
ctgaaaagcc caaaagccaa gatgtag                                      1647
```

<210> SEQ ID NO 5
<211> LENGTH: 10
<212> TYPE: DNA
<213> ORGANISM: Artificial
<220> FEATURE:
<223> OTHER INFORMATION: Kozak sequence for the mammmals

<400> SEQUENCE: 5 gccrccatgg        10

<210> SEQ ID NO 6
<211> LENGTH: 9
<212> TYPE: PRT
<213> ORGANISM: Artificial
<220> FEATURE:
<223> OTHER INFORMATION: conserved sequence

<400> SEQUENCE: 6

Leu Ile Lys Tyr Lys Gly Tyr Gln Val
1               5

<210> SEQ ID NO 7
<211> LENGTH: 23
<212> TYPE: DNA
<213> ORGANISM: Artificial
<220> FEATURE:
<223> OTHER INFORMATION: flexLuc5-ATA primer
<220> FEATURE:
<221> NAME/KEY: misc_feature
<222> LOCATION: (9)..(9)
<223> OTHER INFORMATION: n is a, c, g, or t

<400> SEQUENCE: 7
acytgrtanc cyttatattt aat        23

<210> SEQ ID NO 8
<211> LENGTH: 23
<212> TYPE: DNA
<213> ORGANISM: Artificial
<220> FEATURE:
<223> OTHER INFORMATION: flexLuc5-ATG primer
<220> FEATURE:
<221> NAME/KEY: misc_feature
<222> LOCATION: (9)..(9)
<223> OTHER INFORMATION: n is a, c, g, or t

<400> SEQUENCE: 8
acytgrtanc cyttatattt gat        23

<210> SEQ ID NO 9
<211> LENGTH: 23
<212> TYPE: DNA
<213> ORGANISM: Artificial
<220> FEATURE:
<223> OTHER INFORMATION: flexLuc5-ATT primer
<220> FEATURE:
<221> NAME/KEY: misc_feature
<222> LOCATION: (9)..(9)
<223> OTHER INFORMATION: n is a, c, g, or t

<400> SEQUENCE: 9
acytgrtanc cyttatattt tat                                    23

<210> SEQ ID NO 10
<211> LENGTH: 23
<212> TYPE: DNA
<213> ORGANISM: Artificial
<220> FEATURE:
<223> OTHER INFORMATION: flexLuc5-ACA primer
<220> FEATURE:
<221> NAME/KEY: misc_feature
<222> LOCATION: (9)..(9)
<223> OTHER INFORMATION: n is a, c, g, or t

<400> SEQUENCE: 10
acytgrtanc cyttatactt aat                                    23

<210> SEQ ID NO 11
<211> LENGTH: 23
<212> TYPE: DNA
<213> ORGANISM: Artificial
<220> FEATURE:
<223> OTHER INFORMATION: flexLuc5-ACG primer
<220> FEATURE:
<221> NAME/KEY: misc_feature
<222> LOCATION: (9)..(9)
<223> OTHER INFORMATION: n is a, c, g, or t

<400> SEQUENCE: 11
acytgrtanc cyttatactt gat                                    23

<210> SEQ ID NO 12
<211> LENGTH: 23
<212> TYPE: DNA
<213> ORGANISM: Artificial
<220> FEATURE:
<223> OTHER INFORMATION: flexLuc5-ACT primer
<220> FEATURE:
<221> NAME/KEY: misc_feature
<222> LOCATION: (9)..(9)
<223> OTHER INFORMATION: n is a, c, g, or t

<400> SEQUENCE: 12
acytgrtanc cyttatactt tat                                    23

<210> SEQ ID NO 13
<211> LENGTH: 23
<212> TYPE: DNA
<213> ORGANISM: Artificial
<220> FEATURE:
<223> OTHER INFORMATION: flexLuc5-GTA primer
<220> FEATURE:
<221> NAME/KEY: misc_feature
<222> LOCATION: (9)..(9)
<223> OTHER INFORMATION: n is a, c, g, or t

<400> SEQUENCE: 13
acytgrtanc cyttgtattt aat                                    23

<210> SEQ ID NO 14
<211> LENGTH: 23
<212> TYPE: DNA
<213> ORGANISM: Artificial
<220> FEATURE:
<223> OTHER INFORMATION: flexLuc5-GTG primer
<220> FEATURE:
<221> NAME/KEY: misc_feature
<222> LOCATION: (9)..(9)
<223> OTHER INFORMATION: n is a, c, g, or t

<400> SEQUENCE: 14

```
acytgrtanc cyttgtattt gat                                    23
```

<210> SEQ ID NO 15
<211> LENGTH: 23
<212> TYPE: DNA
<213> ORGANISM: Artificial
<220> FEATURE:
<223> OTHER INFORMATION: flexLuc5-GTT primer
<220> FEATURE:
<221> NAME/KEY: misc_feature
<222> LOCATION: (9)..(9)
<223> OTHER INFORMATION: n is a, c, g, or t

<400> SEQUENCE: 15

```
acytgrtanc cyttgtattt tat                                    23
```

<210> SEQ ID NO 16
<211> LENGTH: 23
<212> TYPE: DNA
<213> ORGANISM: Artificial
<220> FEATURE:
<223> OTHER INFORMATION: flexLuc5-GCA primer
<220> FEATURE:
<221> NAME/KEY: misc_feature
<222> LOCATION: (9)..(9)
<223> OTHER INFORMATION: n is a, c, g, or t

<400> SEQUENCE: 16

```
acytgrtanc cyttgtactt aat                                    23
```

<210> SEQ ID NO 17
<211> LENGTH: 23
<212> TYPE: DNA
<213> ORGANISM: Artificial
<220> FEATURE:
<223> OTHER INFORMATION: flexLuc5-GCG primer
<220> FEATURE:
<221> NAME/KEY: misc_feature
<222> LOCATION: (9)..(9)
<223> OTHER INFORMATION: n is a, c, g, or t

<400> SEQUENCE: 17

```
acytgrtanc cyttgtactt gat                                    23
```

<210> SEQ ID NO 18
<211> LENGTH: 23
<212> TYPE: DNA
<213> ORGANISM: Artificial
<220> FEATURE:
<223> OTHER INFORMATION: flexLuc5-GCT primer
<220> FEATURE:
<221> NAME/KEY: misc_feature
<222> LOCATION: (9)..(9)
<223> OTHER INFORMATION: n is a, c, g, or t

<400> SEQUENCE: 18

```
acytgrtanc cyttgtactt tat                                    23
```

<210> SEQ ID NO 19
<211> LENGTH: 23
<212> TYPE: DNA
<213> ORGANISM: Artificial
<220> FEATURE:
<223> OTHER INFORMATION: GeneRacer5'Primer

<400> SEQUENCE: 19

```
cgactggagc acgaggacac tga                                    23
```

<210> SEQ ID NO 20
<211> LENGTH: 26
<212> TYPE: DNA
<213> ORGANISM: Artificial
<220> FEATURE:
<223> OTHER INFORMATION: GeneRacer5'Nested Primer

<400> SEQUENCE: 20
ggacactgac atggactgaa ggagta                                              26

<210> SEQ ID NO 21
<211> LENGTH: 19
<212> TYPE: DNA
<213> ORGANISM: Artificial
<220> FEATURE:
<223> OTHER INFORMATION: M13-F(-29) Primer

<400> SEQUENCE: 21
cacgacgttg taaaacgac                                                      19

<210> SEQ ID NO 22
<211> LENGTH: 18
<212> TYPE: DNA
<213> ORGANISM: Artificial
<220> FEATURE:
<223> OTHER INFORMATION: M13 Reverse

<400> SEQUENCE: 22
ggataacaat ttcacagg                                                       18

<210> SEQ ID NO 23
<211> LENGTH: 26
<212> TYPE: DNA
<213> ORGANISM: Artificial
<220> FEATURE:
<223> OTHER INFORMATION: Luci5-2-Full-F1 Primer

<400> SEQUENCE: 23
agtattcttg tgcagtgttt aattta                                              26

<210> SEQ ID NO 24
<211> LENGTH: 25
<212> TYPE: DNA
<213> ORGANISM: Artificial
<220> FEATURE:
<223> OTHER INFORMATION: GeneRacer3' Primer

<400> SEQUENCE: 24
gctgtcaacg atacgctacg taacg                                               25

<210> SEQ ID NO 25
<211> LENGTH: 23
<212> TYPE: DNA
<213> ORGANISM: Artificial
<220> FEATURE:
<223> OTHER INFORMATION: GeneRacer3' Nested Primer

<400> SEQUENCE: 25
cgctacgtaa cggcatgaca gtg                                                 23

<210> SEQ ID NO 26
<211> LENGTH: 34
<212> TYPE: DNA
<213> ORGANISM: Artificial
<220> FEATURE:
<223> OTHER INFORMATION: Luci5-2-Full-F2 Primer

<400> SEQUENCE: 26

```
agtattcttg tgcagtgttt aatttaaaga acaa                                34
```

<210> SEQ ID NO 27
<211> LENGTH: 20
<212> TYPE: DNA
<213> ORGANISM: Artificial
<220> FEATURE:
<223> OTHER INFORMATION: T7 promoter Primer

<400> SEQUENCE: 27

```
taatacgact cactataggg                                                20
```

<210> SEQ ID NO 28
<211> LENGTH: 21
<212> TYPE: DNA
<213> ORGANISM: Artificial
<220> FEATURE:
<223> OTHER INFORMATION: T7 Reverse Primer

<400> SEQUENCE: 28

```
ctagttattg ctcagcggtg g                                              21
```

<210> SEQ ID NO 29
<211> LENGTH: 1651
<212> TYPE: DNA
<213> ORGANISM: Luciola sp.

<400> SEQUENCE: 29

```
caccatgaat aatatggatg acggtgaaca catcgtggtt gggcctcaac cattttaccc    60
ggttgaagaa gggtccgctg gcacgcagct gctcaagtac ctgaagcaat attccaaact   120
tggagcgatt gccttttcca atgctcatac taaggtggac atcagctatg cagagtactt   180
ggacaccagc gttcggttgg ctcaggccct gatcaactac ggaatcccta ttgatgggcg   240
gatagccctg tgctcagaga actgtgagga gttttatttt ccagtcctcg ctggattgta   300
cattggtgct ggggtggctc caactaacga aatctacaca ctcagggagc tggtgcactc   360
tctggggata agtaaaccca ctattgtgtt ctcctccaaa aagggactgg agaaggttat   420
caccgttcaa aagacagtga cctgcatcaa aaccatcgtg atcctcgata gcaaggtcga   480
ttatcaaggt tacgactgct tggaaaacctt tataaaaaaa tacctgcctg ccggattcag   540
cgtggagaac tttattccga gagaggtaaa caggaaagaa caggtcgcac tggtcatgaa   600
cagctcaggt agcactgggc tgccgaaagg cgtccaaatt actcatgagg gcgcggtcac   660
gagattctca catgctcgcg atcctatcta tggcaaccag gtttcaccag gcaccgctat   720
tctgacaatt gtcccattcc atcacggctt tgggatgttt accaacctgg gctatctgac   780
ctgcggatac cgcatcgtca tgttgacaaa gttcgatgaa gaactgtttc tcaaaacgct   840
ggccgattat aagtgtactt ctgtgatcct ggtgccaacc ctgtttgcca ttcttagcaa   900
atccgtgttg ctggagaagt atgaccttt caaccttgtt gaaatcgcca gcggtgggc   960
ccctctggcc aaggaagttg gcgaggccgt ggcacgaagg tttaacctgc agggattcg   1020
ccaggggtat gggctgaccg aaacaacaag tgccataatc attactcccg aaggggacga  1080
taaacccgga gcctcaggaa agatcgtgcc tctgttcaga gcgaaggtgg ttgatctgga  1140
cactcagaag actcttggac ctaatagaag gggcgagatc tgcgtgaaag acccatgtt  1200
gatgaagggc tatgtcgatg atccagtcgc cacaagtcaa attatcgaca aggacggctg  1260
gctgcataca ggggatatag gatatttcga tgaggataag cacttcttca tcgtcgaccg  1320
actcaagtcc ctgattaaat acaagggata ccaggtccca cctgcggaac tcgaaagcgt  1380
```

```
cctcctccag catccggaca tctttgatgc aggtgtggcc gggcttccag atccattggc    1440
aggcgaactc ccaggtgccg tcgttgtttt ggagaaaggc cgacacatga ccgaacagca    1500
ggtcatggac tacgtcgcag gtcaagtcag caatgcgaag aggcttcgag gcggcgtgag    1560
attcgtggat gaggtgccga agggactgac cggcaagatc gacagtaagg ccatacgcga    1620
aatcctgaaa agcccaaaag ccaagatgta g                                    1651

<210> SEQ ID NO 30
<211> LENGTH: 1651
<212> TYPE: DNA
<213> ORGANISM: Luciola sp.

<400> SEQUENCE: 30
caccatggat aatatggatg acggtgaaca catcgtggtt gggcctcaac cattttaccc      60
ggttgaagaa gggtccgctg cacgcagct gctcaagtac ctgaagcaat attccaaact     120
tggagcgatt gccttttcca atgctcatac taaggtggac atcagctatg cagagtactt     180
ggacaccagc gttcggttgg ctcaggccct gatcaactac ggaatcccta ttgatgggcg     240
gatagccctg tgctcagaga actgtgagga gttttatttt ccagtcctcg ctggattgta     300
cattggtgct ggggtggctc aactaacga aatctacaca ctcagggagc tggtgcactc      360
tctggggata agtaaaccca ctattgtgtt ctcctccaaa aagggactgg agaaggttat     420
caccgttcaa aagacagtga cctgcatcaa aaccatcgtg atcctcgata gcaaggtcga     480
ttatcaaggt tacgactgct tggaaaacctt tataaaaaaa tacctgcctg ccggattcag     540
cgtggagaac tttattccga gagaggtaaa caggaaagaa caggtcgcac tggtcatgaa     600
cagctcaggt agcactgggc tgccgaaagg cgtccaaatt actcatgagg cgcgcggtcac     660 gagattctca catgctcgcg atcctatcta tggcaaccag gtttcaccag gcaccgctat     720
tctgacaatt gtcccattcc atcacggctt tgggatgttt accaacctgg gctatctgac     780
ctgcggatac cgcatcgtca tgttgacaaa gttcgatgaa gaactgtttc tcaaaacgct     840
ggccgattat aagtgtactt ctgtgatcct ggtgccaacc ctgttttgcca ttcttagcaa     900 atccgtgttg ctggagaagt atgaccttc caaccttgtt gaaatcgcca gcggtgggc      960 ccctctggcc aaggaagttg gcgaggccgt ggcacgaagg tttaacctgc cagggattcg    1020
ccaggggtat gggctgaccg aaacaacaag tgccataatc attactcccg aaggggacga    1080
taaacccgga gcctcaggaa agatcgtgcc tctgttcaga gcgaaggtgg ttgatctgga    1140
cactcagaag actcttggac ctaatagaag gggcgagatc tgcgtgaaag gacccatgtt    1200
gatgaagggc tatgtcgatg atccagtcgc cacaagtcaa attatcgaca aggacggctg    1260
gctgcataca ggggatatag gatatttcga tgaggataag cacttcttca tcgtcgaccg    1320
actcaagtcc ctgattaaat acaagggata ccaggtccca cctgcggaac tcgaaagcgt    1380
cctcctccag catccggaca tctttgatgc aggtgtggcc gggcttccag atccattggc    1440
aggcgaactc ccaggtgccg tcgttgtttt ggagaaaggc cgacacatga ccgaacagca    1500
ggtcatggac tacgtcgcag gtcaagtcag caatgcgaag aggcttcgag gcggcgtgag    1560
attcgtggat gaggtgccga agggactgac cggcaagatc gacagtaagg ccatacgcga    1620
aatcctgaaa agcccaaaag ccaagatgta g                                    1651

<210> SEQ ID NO 31
<211> LENGTH: 48
<212> TYPE: DNA
<213> ORGANISM: Artificial
```

```
<220> FEATURE:
<223> OTHER INFORMATION: Luciola5_D438G

<400> SEQUENCE: 31
gataagcact tcttcatcgt cggccgactc aagtccctga ttaaatac              48

<210> SEQ ID NO 32
<211> LENGTH: 48
<212> TYPE: DNA
<213> ORGANISM: Artificial
<220> FEATURE:
<223> OTHER INFORMATION: Luciola5_I532R

<400> SEQUENCE: 32
ccgaagggac tgaccggcaa gagagacagt aaggccatac gcgaaatc              48

<210> SEQ ID NO 33
<211> LENGTH: 45
<212> TYPE: DNA
<213> ORGANISM: Artificial
<220> FEATURE:
<223> OTHER INFORMATION: Luciola5_E356R

<400> SEQUENCE: 33
agtgccataa tcattactcc cagagggac gataaacccg gagcc                  45

<210> SEQ ID NO 34
<211> LENGTH: 45
<212> TYPE: DNA
<213> ORGANISM: Artificial
<220> FEATURE:
<223> OTHER INFORMATION: Luciola5_V368A

<400> SEQUENCE: 34
cccggagcct caggaaagat cgcccctctg ttcagagcga aggtg                 45

<210> SEQ ID NO 35
<211> LENGTH: 1647
<212> TYPE: DNA
<213> ORGANISM: Luciola sp. mutant 1

<400> SEQUENCE: 35
atgaataata tggatgacgg tgaacacatc gtggttgggc tcaaccatt ttacccggtt    60
gaagaaggt  ccgctggcac gcagctgctc aagtacctga agcaatattc caaacttgga  120
gcgattgcct tttccaatgc tcatactaag gtggacatca gctatgcaga gtacttggac  180
accagcgttc ggttggctca ggccctgatc aactacggaa tccctattga tgggcggata  240
gccctgtgct cagagaactg tgaggagttt attttccag  tcctcgctgg attgtacatt  300
ggtgctgggg tggctccaac taacgaaatc tacacactca gggagctggt gcactctctg  360
gggataagta aacccactat tgtgttctcc tccaaaaagg gactggagaa ggttatcacc  420
gttcaaaaga cagtgacctg catcaaaacc atcgtgatcc tcgatagcaa ggtcgattat  480
caaggttacg actgcttgga aacctttata aaaaatacc tgcctgccgg attcagcgtg  540
gagaactta  ttccgagaga ggtaaacagg aagaacagg tcgcactggt catgaacagc  600
tcaggtagca ctgggctgcc gaaaggcgtc caaattactc atgagggcgc ggtcacgaga  660
ttctcacatg ctcgcgatcc tatctatggc aaccaggttt caccaggcac cgctattctg  720
acaattgtcc cattccatca cggctttggg atgtttacca acctgggcta tctgacctgc  780
ggataccgca tcgtcatgtt gacaaagttc gatgaagaac tgtttctcaa acgctggcc   840
gattataagt gtacttctgt gatcctggtg ccaaccctgt ttgccattct tagcaaatcc  900
```

```
gtgttgctgg agaagtatga cctttccaac cttgttgaaa tcgccagcgg tggggcccct    960
ctggccaagg aagttggcga ggccgtggca cgaaggttta acctgccagg gattcgccag   1020
gggtatgggc tgaccgaaac aacaagtgcc ataatcatta ctcccagagg ggacgataaa   1080
cccggagcct caggaaagat cgtgcctctg ttcagagcga aggtggttga tctggacact   1140
cagaagactc ttggacctaa tagaaggggc gagatctgcg tgaaaggacc catgttgatg   1200
aagggctatg tcgatgatcc agtcgccaca agtcaaatta tcgacaagga cggctggctg   1260
catacagggg atataggata tttcgatgag gataagcact tcttcatcgt cggccgactc   1320
aagtccctga ttaaatacaa gggataccag gtcccacctg cggaactcga aagcgtcctc   1380
ctccagcatc cggacatctt tgatgcaggt gtggccgggc ttccagatcc attggcaggc   1440
gaactcccag gtgccgtcgt tgttttggag aaaggccgac acatgaccga acagcaggtc   1500
atggactacg tcgcaggtca agtcagcaat gcgaagaggc ttcgaggcgg cgtgagattc   1560
gtggatgagg tgccgaaggg actgaccggc aagagagaca gtaaggccat acgcgaaatc   1620
ctgaaaagcc caaaagccaa gatgtag                                       1647

<210> SEQ ID NO 36
<211> LENGTH: 1647
<212> TYPE: DNA
<213> ORGANISM: Luciola sp. mutant 2

<400> SEQUENCE: 36
atgaataata tggatgacgg tgaacacatc gtggttgggc ctcaaccatt ttacccggtt     60 gaagaaggt ccgctggcac gcagctgctc aagtacctga agcaatattc caaacttgga    120
gcgattgcct tttccaatgc tcatactaag gtggacatca gctatgcaga gtacttggac    180
accagcgttc ggttggctca ggccctgatc aactacggaa tccctattga tgggcggata    240
gccctgtgct cagagaactg tgaggagttt tattttccag tcctcgctgg attgtacatt    300
ggtgctgggg tggctccaac taacgaaatc tacacactca gggagctggt gcactctctg    360
gggataagta acccactat tgtgttctcc tccaaaaagg gactggagaa ggttatcacc    420
gttcaaaaga cagtgacctg catcaaaacc atcgtgatcc tcgatagcaa ggtcgattat    480
caaggttacg actgcttgga aacctttata aaaaaatacc tgcctgccgg attcagcgtg    540
gagaacttta ttccgagaga ggtaaacagg aaagaacagg tcgcactggt catgaacagc    600
tcaggtagca ctgggctgcc gaaaggcgtc caaattactc atgagggcgc ggtcacgaga    660
ttctcacatg ctcgcgatcc tatctatggc aaccaggttt caccaggcac cgctattctg    720
acaattgtcc cattccatca cggctttggg atgtttacca acctgggcta tctgacctgc    780
ggataccgca tcgtcatgtt gacaaagttc gatgaagaac tgtttctcaa aacgctggcc    840
gattataagt gtacttctgt gatcctggtg ccaaccctgt ttgccattct tagcaaatcc    900
gtgttgctgg agaagtatga cctttccaac cttgttgaaa tcgccagcgg tggggcccct    960
ctggccaagg aagttggcga ggccgtggca cgaaggttta acctgccagg gattcgccag   1020
gggtatgggc tgaccgaaac aacaagtgcc ataatcatta ctcccagagg ggacgataaa   1080
cccggagcct caggaaagat cgcccctctg ttcagagcga aggtggttga tctggacact   1140
cagaagactc ttggacctaa tagaaggggc gagatctgcg tgaaaggacc catgttgatg   1200
aagggctatg tcgatgatcc agtcgccaca agtcaaatta tcgacaagga cggctggctg   1260
catacagggg atataggata tttcgatgag gataagcact tcttcatcgt cgaccgactc   1320
aagtccctga ttaaatacaa gggataccag gtcccacctg cggaactcga aagcgtcctc   1380
```

-continued

```
ctccagcatc cggacatctt tgatgcaggt gtggccgggc ttccagatcc attggcaggc  1440
gaactcccag gtgccgtcgt tgttttggag aaaggccgac acatgaccga acagcaggtc  1500
atggactacg tcgcaggtca agtcagcaat gcgaagaggc ttcgaggcgg cgtgagattc  1560
gtggatgagg tgccgaaggg actgaccggc aagatcgaca gtaaggccat acgcgaaatc  1620
ctgaaaagcc caaaagccaa gatgtag                                     1647
```

<210> SEQ ID NO 37  
<211> LENGTH: 548  
<212> TYPE: PRT  
<213> ORGANISM: Luciola sp. mutant 1

<400> SEQUENCE: 37

```
Met Asn Asn Met Asp Asp Gly Glu His Ile Val Val Gly Pro Gln Pro
1               5                   10                  15

Phe Tyr Pro Val Glu Glu Gly Ser Ala Gly Thr Gln Leu Leu Lys Tyr
                20                  25                  30

Leu Lys Gln Tyr Ser Lys Leu Gly Ala Ile Ala Phe Ser Asn Ala His
            35                  40                  45

Thr Lys Val Asp Ile Ser Tyr Ala Glu Tyr Leu Asp Thr Ser Val Arg
        50                  55                  60

Leu Ala Gln Ala Leu Ile Asn Tyr Gly Ile Pro Ile Asp Gly Arg Ile
65                  70                  75                  80

Ala Leu Cys Ser Glu Asn Cys Glu Glu Phe Tyr Phe Pro Val Leu Ala
                85                  90                  95

Gly Leu Tyr Ile Gly Ala Gly Val Ala Pro Thr Asn Glu Ile Tyr Thr
                100                 105                 110

Leu Arg Glu Leu Val His Ser Leu Gly Ile Ser Lys Pro Thr Ile Val
            115                 120                 125

Phe Ser Ser Lys Lys Gly Leu Glu Lys Val Ile Thr Val Gln Lys Thr
        130                 135                 140

Val Thr Cys Ile Lys Thr Ile Val Ile Leu Asp Ser Lys Val Asp Tyr
145                 150                 155                 160

Gln Gly Tyr Asp Cys Leu Glu Thr Phe Ile Lys Lys Tyr Leu Pro Ala
                165                 170                 175

Gly Phe Ser Val Glu Asn Phe Ile Pro Arg Glu Val Asn Arg Lys Glu
                180                 185                 190

Gln Val Ala Leu Val Met Asn Ser Ser Gly Ser Thr Gly Leu Pro Lys
            195                 200                 205

Gly Val Gln Ile Thr His Glu Gly Ala Val Thr Arg Phe Ser His Ala
        210                 215                 220

Arg Asp Pro Ile Tyr Gly Asn Gln Val Ser Pro Gly Thr Ala Ile Leu
225                 230                 235                 240

Thr Ile Val Pro Phe His His Gly Phe Gly Met Phe Thr Asn Leu Gly
                245                 250                 255

Tyr Leu Thr Cys Gly Tyr Arg Ile Val Met Leu Thr Lys Phe Asp Glu
                260                 265                 270

Glu Leu Phe Leu Lys Thr Leu Ala Asp Tyr Lys Cys Thr Ser Val Ile
            275                 280                 285

Leu Val Pro Thr Leu Phe Ala Ile Leu Ser Lys Ser Val Leu Leu Glu
        290                 295                 300

Lys Tyr Asp Leu Ser Asn Leu Val Glu Ile Ala Ser Gly Gly Ala Pro
305                 310                 315                 320

Leu Ala Lys Glu Val Gly Glu Ala Val Ala Arg Arg Phe Asn Leu Pro
```

```
                    325                 330                 335
Gly Ile Arg Gln Gly Tyr Gly Leu Thr Glu Thr Thr Ser Ala Ile Ile
                340                 345                 350

Ile Thr Pro Arg Gly Asp Asp Lys Pro Gly Ala Ser Gly Lys Ile Val
            355                 360                 365

Pro Leu Phe Arg Ala Lys Val Val Asp Leu Asp Thr Gln Lys Thr Leu
        370                 375                 380

Gly Pro Asn Arg Arg Gly Glu Ile Cys Val Lys Gly Pro Met Leu Met
385                 390                 395                 400

Lys Gly Tyr Val Asp Asp Pro Val Ala Thr Ser Gln Ile Ile Asp Lys
                405                 410                 415

Asp Gly Trp Leu His Thr Gly Asp Ile Gly Tyr Phe Asp Glu Asp Lys
            420                 425                 430

His Phe Phe Ile Val Gly Arg Leu Lys Ser Leu Ile Lys Tyr Lys Gly
        435                 440                 445

Tyr Gln Val Pro Pro Ala Glu Leu Glu Ser Val Leu Leu Gln His Pro
    450                 455                 460

Asp Ile Phe Asp Ala Gly Val Ala Gly Leu Pro Asp Pro Leu Ala Gly
465                 470                 475                 480

Glu Leu Pro Gly Ala Val Val Leu Glu Lys Gly Arg His Met Thr
                485                 490                 495

Glu Gln Gln Val Met Asp Tyr Val Ala Gly Gln Val Ser Asn Ala Lys
            500                 505                 510

Arg Leu Arg Gly Gly Val Arg Phe Val Asp Glu Val Pro Lys Gly Leu
        515                 520                 525

Thr Gly Lys Arg Asp Ser Lys Ala Ile Arg Glu Ile Leu Lys Ser Pro
    530                 535                 540

Lys Ala Lys Met
545

<210> SEQ ID NO 38
<211> LENGTH: 548
<212> TYPE: PRT
<213> ORGANISM: Luciola sp. mutant 2

<400> SEQUENCE: 38

Met Asn Asn Met Asp Asp Gly Glu His Ile Val Val Gly Pro Gln Pro
1               5                   10                  15

Phe Tyr Pro Val Glu Glu Gly Ser Ala Gly Thr Gln Leu Leu Lys Tyr
            20                  25                  30

Leu Lys Gln Tyr Ser Lys Leu Gly Ala Ile Ala Phe Ser Asn Ala His
        35                  40                  45

Thr Lys Val Asp Ile Ser Tyr Ala Glu Tyr Leu Asp Thr Ser Val Arg
    50                  55                  60

Leu Ala Gln Ala Leu Ile Asn Tyr Gly Ile Pro Ile Asp Gly Arg Ile
65                  70                  75                  80

Ala Leu Cys Ser Glu Asn Cys Glu Glu Phe Tyr Phe Pro Val Leu Ala
                85                  90                  95

Gly Leu Tyr Ile Gly Ala Gly Val Ala Pro Thr Asn Glu Ile Tyr Thr
            100                 105                 110

Leu Arg Glu Leu Val His Ser Leu Gly Ile Ser Lys Pro Thr Ile Val
        115                 120                 125

Phe Ser Ser Lys Lys Gly Leu Glu Lys Val Ile Thr Val Gln Lys Thr
    130                 135                 140

Val Thr Cys Ile Lys Thr Ile Val Ile Leu Asp Ser Lys Val Asp Tyr
```

```
                145                 150                 155                 160
Gln Gly Tyr Asp Cys Leu Glu Thr Phe Ile Lys Lys Tyr Leu Pro Ala
                165                 170                 175
Gly Phe Ser Val Glu Asn Phe Ile Pro Arg Glu Val Asn Arg Lys Glu
                180                 185                 190
Gln Val Ala Leu Val Met Asn Ser Ser Gly Ser Thr Gly Leu Pro Lys
                195                 200                 205
Gly Val Gln Ile Thr His Glu Gly Ala Val Thr Arg Phe Ser His Ala
                210                 215                 220
Arg Asp Pro Ile Tyr Gly Asn Gln Val Ser Pro Gly Thr Ala Ile Leu
225                 230                 235                 240
Thr Ile Val Pro Phe His His Gly Phe Gly Met Phe Thr Asn Leu Gly
                245                 250                 255
Tyr Leu Thr Cys Gly Tyr Arg Ile Val Met Leu Thr Lys Phe Asp Glu
                260                 265                 270
Glu Leu Phe Leu Lys Thr Leu Ala Asp Tyr Lys Cys Thr Ser Val Ile
                275                 280                 285
Leu Val Pro Thr Leu Phe Ala Ile Leu Ser Lys Ser Val Leu Leu Glu
                290                 295                 300
Lys Tyr Asp Leu Ser Asn Leu Val Glu Ile Ala Ser Gly Gly Ala Pro
305                 310                 315                 320
Leu Ala Lys Glu Val Gly Glu Ala Val Ala Arg Arg Phe Asn Leu Pro
                325                 330                 335
Gly Ile Arg Gln Gly Tyr Gly Leu Thr Glu Thr Thr Ser Ala Ile Ile
                340                 345                 350
Ile Thr Pro Arg Gly Asp Asp Lys Pro Gly Ala Ser Gly Lys Ile Ala
                355                 360                 365
Pro Leu Phe Arg Ala Lys Val Val Asp Leu Asp Thr Gln Lys Thr Leu
                370                 375                 380
Gly Pro Asn Arg Arg Gly Glu Ile Cys Val Lys Gly Pro Met Leu Met
385                 390                 395                 400
Lys Gly Tyr Val Asp Asp Pro Val Ala Thr Ser Gln Ile Ile Asp Lys
                405                 410                 415
Asp Gly Trp Leu His Thr Gly Asp Ile Gly Tyr Phe Asp Glu Asp Lys
                420                 425                 430
His Phe Phe Ile Val Asp Arg Leu Lys Ser Leu Ile Lys Tyr Lys Gly
                435                 440                 445
Tyr Gln Val Pro Pro Ala Glu Leu Glu Ser Val Leu Leu Gln His Pro
                450                 455                 460
Asp Ile Phe Asp Ala Gly Val Ala Gly Leu Pro Asp Pro Leu Ala Gly
465                 470                 475                 480
Glu Leu Pro Gly Ala Val Val Val Leu Glu Lys Gly Arg His Met Thr
                485                 490                 495
Glu Gln Gln Val Met Asp Tyr Val Ala Gly Gln Val Ser Asn Ala Lys
                500                 505                 510
Arg Leu Arg Gly Gly Val Arg Phe Val Asp Glu Val Pro Lys Gly Leu
                515                 520                 525
Thr Gly Lys Ile Asp Ser Lys Ala Ile Arg Glu Ile Leu Lys Ser Pro
                530                 535                 540
Lys Ala Lys Met
545
```

FIREFLY LUCIFERASE

CROSS REFERENCE TO RELATED APPLICATIONS

This application is a Continuation Application of PCT Application No. PCT/JP2011/054841, filed Feb. 24, 2011 and based upon and claiming the benefit of priority from prior Malaysian Patent Application No. PI 2010000839, filed Feb. 25, 2010, the entire contents of all of which are incorporated herein by reference.

BACKGROUND OF THE INVENTION

1. Field of the Invention

The present invention relates to a firefly luciferase. More specifically, it relates to a firefly luciferase which emits light at high luminosity, the variants thereof, and a method for determining function of a cell by expressing a gene of the luciferase in a cell and detecting the light emission by means of imaging.

2. Description of the Related Art

For determining function of cells such as intracellular signal transduction and gene expression, a fluorescent probe such as a fluorescent dye and fluorescent protein and a luminescence probe utilizing luciferine-luciferase reaction have been used. Especially, for the analysis of gene expression regulation, luminescence measurement, which does not cause damage of cell due to exciton light, dose not cause autofluorescence and is excellent in terms of quantitative determination, is used. For example, in the case of observing a cell to which luciferase gene is introduced, the intensity of expression of the luciferase gene (more specifically, the expression amount) can be determined by measuring the luminescence from the cell by luciferase. The measurement of the luminescence is performed by the procedures in which luciferine, ATP, and the like are added to a lysate prepared by lysis of cells, and the solution is subjected to a quantitative determination by a luminometer utilizing a photoelectric multiplier. Namely, the degree of luminescence is measured after lysis of cells, and thus the expression amount of luciferase gene at a certain time point is determined as an average value of the entire cell. Examples of a method for introducing a luminescence gene such as luciferase gene as a reporter gene are a calcium phosphate method, lipofection, and electroporation, and each of these methods is used in accordance with the purpose and type of cells. Analysis of the expression amount of luciferase with use of an objective DNA fragment ligated to the upstream or downstream of luciferase gene to be introduced into a cell enables study of the effect of the DNA fragment on transcription of luciferase gene. Further, co-expression of luciferase gene to be introduced into a cell and the objective gene enables study of the effect of the gene product on expression of luciferase gene.

For time-course analysis of the expression amount of a luminescence gene, the degree of luminescence of a living cell needs to be measured over time. Such measurement is carried out by cell cultivation in an incubator provided with a luminometer and quantitative determination of the degree of luminescence from the whole cell population every one hour. Consequently, an expression rhythm etc. having a certain cycle can be analyzed, and the time course of the expression amount of the luminescence gene in the entire cell can be obtained.

In recent years, in a field of biology and medical science there is increasing necessity of the time course observation of dynamic alterations in living samples with images. In a field of utilizing observation of fluorescence, time lapse or dynamic image pickup has been adopted for understanding function of a protein molecular dynamically. In the conventional technique, time course observation with use of a fluorescent sample has been carried out, for example, observation of moving images for one molecule of a protein provided with an added fluorescent molecule.

In contrast, when a luminescent sample is used for time-course observation, use of a CCD camera equipped with an image intensifier is required since the luminescent intensity of the luminescent sample is extremely low. Recently, a microscope equipped with an optical system for observation of luminescent samples has been developed (Jpn. Pat. Appln. KOKAI Publication No. 2006-301599, International Publication No. 2006/088109).

Upon image pickup of a luminescent sample having small luminescent intensity, it should be exposed for a longer term for obtaining clear image. Such a luminescent sample is used for only limited research. For example, when 30 minutes of exposure is required because of low luminescent intensity, time-course image pickup is possible at every 30 minutes but is not at a shorter time interval, and real-time image pickup is also impossible. Plural images should be obtained and compared in order to focus on cells which emit light, and thus when longer exposure time is required because of low luminescent intensity, it is time-consuming.

BRIEF SUMMARY OF THE INVENTION

The object of the present invention is provision of luciferase indicating high luminescence in comparison to the conventional firefly luciferase.

The luciferase of the present invention is characterized by being derived from Malaysian fireflies belonging to genus *Luciola*.

The luciferase of the present invention is characterized by having a maximum luminescent wavelength of 580 nm at pH 8.

The luciferase of the present invention is characterized by indicating 23.3 times or more of luminescent intensity in comparison to that of Rhodamine 6G.

According to the present invention, luciferase having higher luminescent intensity than that of conventional firefly luciferase is provided, and thus detection is possible even with a minute amount of luciferase, thereby the exposure time necessary for luminescent image pickup can be shorten and the time-course observation with higher time resolution can be achieved compared to that of the conventional technique.

BRIEF DESCRIPTION OF THE SEVERAL VIEWS OF THE DRAWING

FIG. 1 shows emission spectra of SP1 luciferase at various pHs.

FIG. 2 illustrates Km values with respect to various luciferases.

FIG. 5 shows temporal change of luminescence intensity of original SP1 luciferase and two types of mutants.

FIG. 6 shows temporal change of luminescence intensity of hRluc luciferase used as an internal standard.

DETAILED DESCRIPTION OF THE INVENTION

The present invention relates to luciferase derived from Malaysian *Luciola* fireflies.

"Luciferase" is a class of enzyme which catalyzes a luminescent chemical reaction. The substrate of this enzyme is called as luciferin. In the presence of ATP, emission of light occurs upon chemical reaction of luciferin because of the catalytic activity of luciferase. Presently, luciferases derived from fireflies and bacteria have been obtained. The luciferase of the present invention also indicates those defined above, but is novel one which has been first obtained from the firefly described below.

The luciferase of the present invention is derived from Malaysian fireflies belonging to the genus *Luciola*. The fireflies are native mainly to Malaysia, and include those which have been only proved to belong to the genus *Luciola*, although a scientific name has not yet been assigned. Here, the term "derive" means to contain not only wild-type luciferases from Malaysian *Luciola* fireflies but also variants thereof.

The luciferase of the present invention indicates remarkably high luminescent intensity in comparison to known luciferases. Thus, the luciferase of the present invention exhibits a particularly advantageous effect when it is used as a reporter for imaging of proteins. More specifically, the luciferase of the present invention enables excellent detection of proteins whose expression amount is small since it can provide a high degree of luminescence even with a small amount. The luciferase of the present invention is capable of reducing the exposure time which is necessary for detection, because of high luminescent intensity. Therefore, it enables the reduction of the interval between image pickups by utilizing the luciferase of the present invention as a reporter for time-course observation, thereby achieving observation which is closer to real-time observation.

An example of the luciferase of the present invention is those containing the amino acid sequence represented by SEQ ID NO: 1. The luciferase has been obtained from fireflies inhabiting mainly in Malaysia for which a scientific name has not been assigned although it has been proved to belong to the genus *Luciola*. In the disclosure, the fireflies are referred to as *Luciola* sp1, and the luciferase derived from the fireflies is referred to as SP1 luciferase.

FIG. 1 indicates luminescence spectra of the luciferase of the present invention. As is shown by the figure, the luciferase of the present invention has a maximum wavelength of 580 nm at pH 8.

Figure 3:
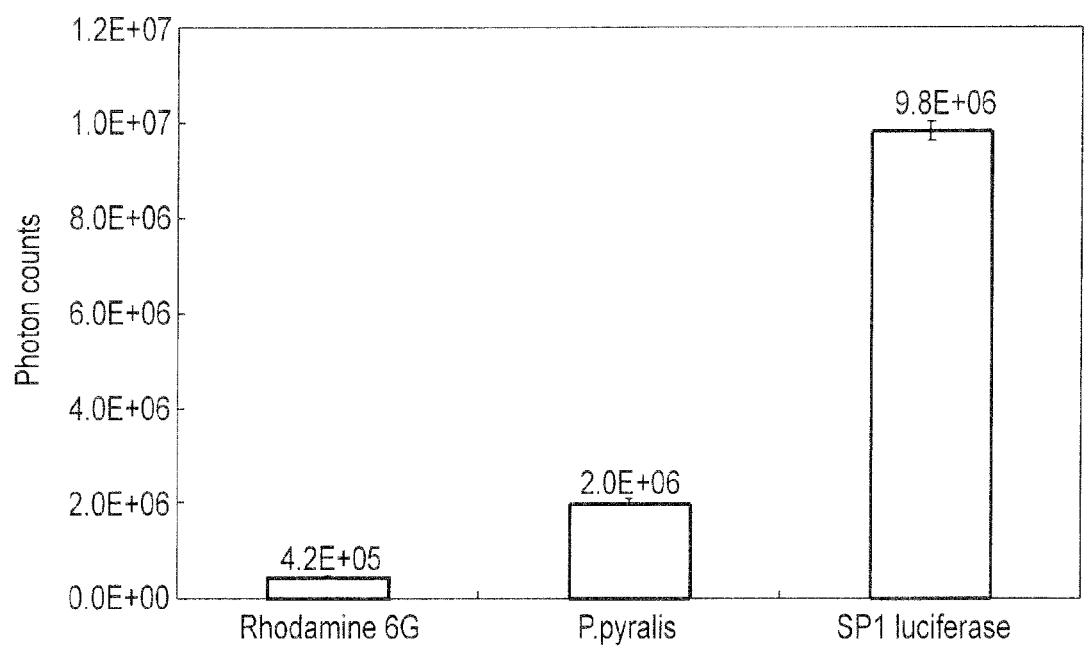
FIG. 3 compares SP1 luciferase, *P. pyralis* luciferase, and Rhodamine 6G with respect to luminescent intensity.

In FIG. 3, luminescent intensity of SP1 luciferase is compared to those of other luminescent substances. This figure indicates that SP1 luciferase has s23.3 times or more of luminescent intensity in comparison to that of Rhodamine 6G. The luminescent intensity has been obtained by integration of light of between 300 nm and 650 nm for ten seconds. As is shown by the figure, the luciferase of the present invention has higher luminescent intensity in comparison to known luminescent substances and conventional firefly luciferases. The luciferase of the present invention indicates preferably, 5 times or more, 10 times or more, 20 times or more, 21 times or more, 22 times or more, or 23 times or more of luminescent intensity in comparison to that of Rhodamine 6G.

The luciferase of the present invention includes not only those of wild type which is derived from Malaysian *Luciola* fireflies, but also variant luciferases in which a part of the amino acid sequence of wild-type luciferase is mutated. Such mutation may be those which improve the enzymatic activity thereof. Such mutation may be those which improve experimental operability thereof. For example, when wild-type luciferase indicates a low solubility in a mammal cell, the variant luciferase of the present invention may be those to which mutation increasing the solubility thereof is introduced. Here, the variant luciferase may be those containing mutations in the amino acid sequence, for example, substitution, deletion, and/or addition of amino acids, as long as it indicates the characteristics of the luciferase of the present invention, that is, higher luminescent intensity in comparison to conventional luciferases. The mutation is those of at least one of amino acid sequence of the wild-type luciferase, and preferably those of from 1 to 20, from 1 to 15, from 1 to 10, or 1 to 5 amino acids of the wild-type luciferase. Preferably, amino acid sequence of variant luciferases has homology of 75% or more, 80% or more, 85% or more, 90% or more, 95% or more, 96% or more, 97% or more, 98% or more, or 99% or more with amino acid sequence of the wild-type luciferase.

The present invention relates to a nucleic acid containing the base sequence encoding the luciferase of the present invention. Namely, the nucleic acid contains luciferase gene which is derived from Malaysian *Luciola* fireflies. In the present invention, a nucleic acid indicates, for example, DNA or RNA. In the present invention, a "gene" of luciferase means mainly a region transcribed by mRNA, that is, a structural gene.

An example of a nucleic acid containing base sequence encoding the luciferase of the present invention is a nucleic acid containing the base sequence represented by SEQ ID NO: 2. The gene having this sequence is cloned from *Luciola* sp1 and encodes SP1 luciferase.

The nucleic acid of the present invention may be those containing base sequence of the wild-type luciferase gene and those containing base sequence of the variant luciferase gene having a mutation therein. Here, the variant luciferase gene may be a gene in which specific bases in the base sequence, for example, several bases are substituted, deleted, and/or added, as long as it can exhibit the characteristics, that is, higher luminescent intensity in comparison to conventional luciferases. Mutation of base sequence includes those which do not cause alteration of the amino acid sequence to be encoded. Namely, the nucleic acid of the present invention includes those containing a mutated luciferase gene which encodes wild-type luciferase.

An example of mutation which does not cause alternation of the amino acid sequence to be encoded is mutation which cancels recognition sequence of a specific restriction enzyme. Because of this mutation, the nucleic acid containing the gene is not digested by the restriction enzyme, but the gene can encode the protein having the same amino acid sequence as that of before mutation. Such mutation can be achieved by conversion of the codons constituting the recognition sequence of the restriction enzyme to the synonymous codons. Such mutation is useful when the recognition sequence of the restriction enzyme to be used for genetic recombination is in the gene. In this case, fragmentation of the nucleic acid can be prevented by canceling the recognition sequence of the gene in advance, thereby facilitating genetic recombination. An example of such a base sequence is that represented by SEQ ID NO: 3. In the sequence, the recognition sequences of BamHI and EcoRI are cancelled.

Another example of mutation which does not cause alteration of an amino acid to be coded is mutation which optimizes codons of a gene for expression in a specific organism species. Here, the term "optimization" means to substitute codons of a gene contained in a nucleic acid with codons which has high codon frequency in a specific organism species. If the optimization is carried out, expression of a gene in a specific organism species is enhanced in comparison to the case without optimization. The luciferase gene of the present invention is derived from fireflies, and thus as the organism species to which the gene is introduced is farther from fireflies in terms of taxonomy, the higher effects can be obtained by optimization. In the present invention, a specific organism species is, for example, a bacterial cell, yeast cell, and mammal cell. A mammal cell is, for example, a mouse cell, monkey cell, and human cell.

An example of the nucleic acid of the present invention containing the base sequence in which codons are optimized and which encodes luciferase, is a nucleic acid containing the base sequence represented by SEQ ID NO: 4. In the nucleic acid, the recognition sequences of BamHI and EcoRI are cancelled and codons are optimized for expression in a mammal cell.

The nucleic acid of the present invention contains those containing luciferase gene provided with Kozak sequence. Kozak sequence is sequence comprised of initiation codon and plural base sequences located in before and after the initiation codon. It has been proved that expression amount of the gene is increased because of presence of Kozak sequence. With respect to Kozak sequence, common sequence has been found in each organism species or biome. The nucleic acid containing Kozak sequence of the present invention has Kozak sequence corresponding to the organism species to which it is introduced. For example, in the case where it is introduced into a mammal cell, the nucleic acid contains sequence gccrccatgg (SEQ ID NO: 5) as Kozak sequence, in which r means guanine or adenine. Luciferase gene provided with Kozak sequence may be a wild-type gene and variant gene in which codons are optimized in such a manner described above. An example of the nucleic acid of the present invention containing luciferase gene sequence provided with Kozak sequence is a nucleic acid containing base sequence represented by SEQ ID NO: 29 or a nucleic acid containing base sequence represented by SEQ ID NO: 30. In these nucleic acids, the recognition sequences of BamHI and EcoRI are cancelled, codons is optimized corresponding to a mammal cell, and Kozak sequence corresponding to a mammal cell is provided.

The present invention contains a vector having these nucleic acids. The vector may contain a nucleic acid and the like containing sequence for regulating expression or sequence of a marker gene other than the nucleic acid encoding luciferase.

The present invention contains a luminescence probe. The luminescence probe may contain wild-type luciferase or the variant thereof. Preferably, the probe is modified by conventional techniques to improve the utilization of the probe. Further, the luminescence probe of the present invention may be applied for various purposes (imaging, photometry, luminometer and the like) with regard to various in vivo samples or in vitro samples.

The present invention relates to a method for analyzing function in a cell by utilizing the luciferase of the present invention. The method comprises introducing the luciferase of the present invention into a cell and detecting luminescence of the luciferase with an imaging apparatus. For example, the luciferase gene of the present invention is introduced in downstream of a specific expression regulation region in DNA, and the expression of luciferase is detected based on the presence or absence of luminescence, thereby achieving the determination of the function of the expression regulation region.

The present invention relates to a method for analyzing an intracellular protein utilizing the luciferase of the present invention. The method comprises introducing a fusion protein comprised of luciferase of the present invention and a protein to be analyzed and; and detecting luminescence of the luciferase with an imaging apparatus.

The method contains observation of localization of the protein to be analyzed in a cell and time-course observation (time-lapse) of the localization. The method contains not only the protein localization but also mere confirmation whether the protein is expressed or not. Cells to be used are nonexclusive, and may be those which can be ordinarily used in a field of cell imaging. Further, the proteins to be analyzed are also nonexclusive, and they can be selected in accordance with the aim of research. The protein may be those which essentially exist in a cell to be used, or may be heterogeneous or modified proteins which are do not essentially exist in a cell.

Upon introducing a fusion protein into a cell, known methods for introducing can be applied. One of them is a method for directly introducing a fusion protein purified in vitro into a cell. For example, a fusion protein can be directly injected into a cell by a microinjection method. Or, a cell is incubated in culture medium containing a fusion protein, thereby introducing the fusion protein into a cell by endocytosis. Another method is to introduce a nucleic acid containing the base sequence encoding the fusion protein, followed by expression of the fusion protein in a cell. For example, an expression vector containing the nucleic acid is introduced into a cell by a calcium phosphate method, lipofection, electroporation, and the like, thereby achieving expression of the fusion protein from the expression vector. Here, the gene of a fusion protein is those containing the luciferase gene of the present invention and the gene of the protein to be analyzed, in which the luciferase gene and the gene of the protein are linked so that each of them can be normally translated.

Upon detection of luminescence of luciferase with an imaging apparatus, well known detection methods can be applied. For example, luciferase luminescent reaction is caused by adding luciferin, ATP, $Mg^{2+}$ ions, and the like are added to a cell expressing a fusion protein containing lucifarese as appropriate, and the luminescence caused can be detected by an imaging apparatus. The imaging apparatus is a microscope provided with a filter for capturing luminescence. The localization of a protein can be specified by using a microscope based on the information obtained through identification of position of luminescence in a cell. As an imaging apparatus, a microscope provided with function which enables time-course image pickup can be used, and time-course observation can be achieved by the microscope.

EXAMPLE 1

Cloning of Luciferase Gene

1. Materials

Firefly larvae collected in the state of Perak were used as materials. The used firefly has been proved to belong to genus *Luciola*, but a scientific name has not been assigned thereto. In this disclosure, the species is referred to as *Luciola* sp1.

2. Extraction of Total RNA and Synthesis of cDNA

A luminescent organ was cut off from firefly larvae. To Lysing Matrix D tube (MP-Biomedicals, LLP), which is a tube containing beads for homogenizing tissues and cells, added were the collected luminescent organ and 1 mL of total RNA extraction reagent TRIzol Reagent (Invitrogen). The tube was installed in a homogenization system FastPrep 24 (MP-Biomedicals, LLP) or FastPrep FP100A (MP-Biomedicals Co., Ltd.), and the firefly luminescent organ was homogenized in the reagent at speed of 6.5 m/s and time of 45 seconds. Upon completion thereof, the tube was taken out from the system and placed on ice for 30 minutes. Consequently, the homogenizing process was repeated once under the same condition.

In the next step, according to the instructions of total RNA extraction reagent TRIzol Reagent, total RNA was isolated and purified from the homogenized solution. 100 μl of the obtained mRNA solution was precipitated and concentrated by an ethanol precipitation method. From a full length cDNA was synthesized from the precipitated and concentrated total RNA with use of a full length cDNA synthesis reagent GeneRacer (Invitrogen) according to the manual. 20 μl of the obtained cDNA solution was subjected to the genetic experiments described below as a firefly full length cDNA library.

3. Identification of 5' Terminal Side of Firefly Luciferase Gene 3-1. Preparation of Primers to be Used for Rapid Amplification of cDNA End (RACE) Method Cloning of a novel luciferase gene was performed by a polymerase chain reaction (PCR) method. The primers used for the PCR were prepared as described below based on the amino acid sequence of luciferase from a known closely-related species.

In order to confirm the amino acid region which is highly conserved in firefly luciferases, amino acid sequences of 10 types of firefly luciferase which have been already published are compared to one another with use of sequence information analysis software DNASIS Pro (Hitachi Software Engineering Co., Ltd.). The closely-related species used for the comparison is *Lampyris noctiluca* (Registration No. CAA61668), *Luciola cruciata* (Registration No. P13129), *Luciola lateralis* (Registration No. Q00158), *Luciola mingrelica* (Registration No. Q26304), *Hotaria parvula* (Registration No. AAC37253), *Photinus pyralis* (Registration No. BAF48390), *Photuris pennsylvanica* (Registration No. Q27757), *Pyrocoelia miyako* (Registration No. AAC37254), *Pyrocoelia rufa* (Registration No. AAG45439), and *Rhagophthalmus ohbai* (Registration No. BAF34360).

Consequently, it was proved that amino acid sequence L-I-K-Y-K-G-Y-Q-V (SEQ ID NO: 6) located in the proximity of 440th residue on C terminal side of firefly luciferase is highly conserved. Based on the codons encoding these 9 amino acids, the base sequence was predicted, and 12 types of firefly luciferase specific mixed primers were designed to be applied to 5' terminal RACE PCR. The names and sequences of these primers are: flexLuc5-ATA (5'-ACY TGR TAN CCY TTA TAT TTA AT-3': SEQ ID NO: 7), flexLuc5-ATG (5'-ACY TGR TAN CCY TTA TAT TTG AT-3': SEQ ID NO: 8), flexLuc5-ATT (5'-ACY TGR TAN CCY TTA TAT TTT AT-3': SEQ ID NO: 9), flexLuc5-ACA (5'-ACY TGR TAN CCY TTA TAC TTA AT-3': SEQ ID NO: 10), flexLuc5-ACG (5'-ACY TGR TAN CCY TTA TAC TTG AT-3': SEQ ID NO: 11), flexLuc5-ACT (5'-ACY TGR TAN CCY TTA TAC TTT AT-3': SEQ ID NO: 12), flexLuc5-GTA (5'-ACY TGR TAN CCY TTG TAT TTA AT-3': SEQ ID NO: 13), flexLuc5-GTG (5'-ACY TGR TAN CCY TTG TAT TTG AT-3': SEQ ID NO: 14), flexLuc5-GTT (5'-ACY TGR TAN CCY TTG TAT TTT AT-3': SEQ ID NO: 15), flexLuc5-GCA (5'-ACY TGR TAN CCY TTG TAC TTA AT-3': SEQ ID NO: 16), flexLuc5-GCG (5'-ACY TGR TAN CCY TTG TAC TTG AT-3': SEQ ID NO: 17), flexLuc5-GCT (5'-ACY TGR TAN CCY TTG TAC TTT AT-3': SEQ ID NO: 18); Y, R, and N in the primer sequences indicating mixed bases. The synthesis of these primers was commissioned to Life Technologies, Japan, Co., Ltd.

3-2. Cloning of 5' Terminal Side of Firefly Luciferase Gene by 5'-RACE PCR

With use of the firefly full-length cDNA library which was prepared in such a manner described above as a template, 5'-RACE RCP was performed using 12 types of specific mixed primers prepared in such a manner described above; GeneRacer5'Primer (5'-CGA CTG GAG CAC GAG GAC ACT GA-3': SEQ ID NO: 19) and GeneRacer5'Nested Primer (5'-GGA CAC TGA CAT GGA CTG AAG GAG TA-3': SEQ ID NO: 20). GeneRacer5' Primer and GeneRacer5' Nested Primer were those contained in a full length cDNA synthesis reagent GeneRacer kit (Invitrogen). In order to amplify the luciferase gene efficiently by 5'-RACE PCR, with use of the gene amplified once by PCR as a template, nested PCR which amplifies the gene further specifically with an inside primer pair was performed. The PCR was carried out with use of polymerase Ex-Taq (Takara Bio Inc.) according to the manual.

As the first PCR, the luciferase gene was amplified with use of 12 types of primer pairs composed of any one of the aforementioned 12 types of specific mixed primer and GeneRacer5' Primer. To 10 μl of PCR reaction solution comprising 10× Ex Tag Buffer diluted tenfold (20 mM $Mg^{2+}$ plus), dNTP Mixture at a final concentration of 0.2 mM (2.5 mL for each base), TaKaRa Ex Taq (5 U/μl) at a final concentration of 0.05 U/μl, one of 12 types of primers at a final concentration of 1.0 μM, and GeneRacer3' Primer at a final concentration of 0.3 μM, added was 0.2 μl of firefly full-length cDNA library solution. Here, the concentration of the firefly full-length cDNA library solution was not determined. In the PCR reaction, the solution was thermally denatured for 2 minutes at 94° C., and then the cycle consisting of 30 seconds at 94° C., 30 seconds at 45° C., and 90 seconds at 72° C. was repeated 30 times, followed by an elongation reaction at 72° C. for 5 minutes. After the PCR reaction, 1 μl of the PCR reaction solution was applied to 1% tris acetic acid buffer (TAE) agarose gel electrophoresis, and observed bands of amplified genes under exposure of ultraviolet after dyeing with ethidium bromide. In all of the 12 reaction solution, a slight gene amplification was confirmed, and thus a nested PCR reaction was carried out with use of each PCR reaction solution as a template, in such a manner described below.

As nested PCR, amplification of luciferase gene was carried out with use of four kinds of primer pairs each consisting of one of four types out of 12 types of primers used in the first PCR and GeneRacer3' Nested Primer. To 10 μl of PCR reaction solution comprising 10× Ex Tag Buffer (20 mM $Mg^{2+}$ plus) diluted tenfold, dNTP Mixture at a final concentration of 0.2 mM (2.5 mL for each base), TaKaRa Ex Taq (5 U/μl) at a final concentration of 0.05 U/μl, one of 12 types of primers at a final concentration of 1.0 μM, and GeneRacer3' Primer at a final concentration of 0.3 μM, added was 10 μl of the first PCR reaction solution diluted ten fold with sterilized water as a template. In the PCR reaction, the solution was thermally denatured for 2 minutes at 94° C., and then the cycle consisting of 30 seconds at 94° C., 30 seconds at 45° C., and 90 seconds at 72° C. was repeated 30 times, followed by an elongation reaction at 72° C. for 5 minutes. After the PCR reaction, 1 μl of PCR reaction solution was applied to 1% tris acetic acid buffer (TAE) agarose gel electrophoresis, and observed bands of amplified genes under exposure of ultraviolet after dyeing with ethidium bromide. The combination condition of primers which efficiently amplified the gene in the proximity of about 1.4 kbp was confirmed.

3-3. Determination of Base Sequence of Gene Amplified by 5'-RACE

In order to determine the base sequence of the gene amplified by 5'-RACE, purification by gel extraction, subcloning, and direct sequencing were carried out. The details are given below.

The PCR was carried out with use of the combination which efficiently amplified the gene in proximity of 1.4 kbp was performed (final volume 20 µl), and then the objective gene fragments were collected with use of gel extraction. Gel extraction was carried out with use of Wizard SV Gel and PCR Clean-UP System (Promega KK) according to the manual thereof. Subcloning of the PCR products extracted from gel were carried out by means of TA cloning. TA cloning was carried out with use of pGEM-T Easy Vector System (Promega KK) according to the manual thereof. Subsequently, the vector DNA was transformed to *Escherichia coli* (TOP10 strain or DH5α strain), and insert-positive colonies were selected by means of blue-white screening. The selected colonies were subjected to a direct colony PCR, and confirmed that the objective gene was inserted. In a direct colony PCR, a primer pair consisting of M13-F(-29) Primer (5'-CAC GAC GTT GTA AAA CGA C-3': SEQ ID NO: 21) and M13 Reverse (5'-GGA TAA CAA TTT CAC AGG-3': SEQ ID NO: 22) was used. To 10 µl of PCR reaction solution comprising 10× Ex Taq Buffer (20 mM $Mg^{2+}$ plus) diluted tenfold, dNTP Mixture at a final concentration of 0.2 mM (2.5 mL for each base), TaKaRa Ex Taq (5 U/µl) at a final concentration of 0.05 U/µl, and a primer pair at a final concentration of 0.2 µM, added was a small amount of colony of Escherichia coli. In the PCR reaction, the solution was thermally denatured for 1 minute at 94° C., and then the cycle consisting of 30 seconds at 94° C., 30 seconds at 50° C., and 2 minutes at 72° C. was repeated 25 times, followed by an elongation reaction at 72° C. for 2 minutes. After the PCR reaction, 2 µl of PCR reaction solution was applied to 1% TAE agarose gel electrophoresis, and observed bands of amplified genes under exposure of ultraviolet after dyeing with ethidium bromide.

With regard to the PCR reaction solution for which amplification was confirmed, the base sequence of the gene was determined by means of a direct sequencing method. With use of PCR product purification kit ExoSAP-IT (GE Healthcare Bioscience), the extra dNTP and primers contained in the PCR reaction solution was removed, and a template for the PCR direct sequencing was prepared. With use of BigDye Terminator v3.1 Cycle Sequencing Kit (Applied Biosystems), a sequencing reaction solution containing the template was prepared, and a sequencing reaction was performed by a thermal cycler. Purification and sequencing of the PCR products were each carried according to the manuals thereof. After the sequencing reaction, the reaction products were purified as described below. 2.5 times of weight of 100% ethanol was added to the reaction solution, and then a nucleic acid was precipitated by a centrifuge. After the supernatant was removed, the precipitate was dried. To the purified precipitate, 15 µl of Hi-Di Formanmide (Applied Biosystems) was added and dissolved. The solution was subjected to thermal denaturation at 94° C. for 2 minutes, and further rapidly cooled on ice, thereby providing a sample for determination of base sequence. With respect to the sample, the base sequence was determined by using Applied Biosystems 3130X1 genetic analyzer (Applied Biosystems). The analytical method was carried out according to the manual.

The obtained gene sequence was analyzed by the "sequence linking" function of sequence information analysis software DNASIS Pro. With respect to the sequence, homology research was performed by using blastx search provided by the National Center for Biotechnology Information (NCBI), and it was confirmed that the sequence indicates a high homology with base sequences of known firefly luciferases. The base sequence obtained by the aforementioned experiments and analyses was determined as being located on 5' terminal side of a novel firefly luciferase gene.

4. 3' Race RCR of Firefly Luciferase Gene and Acquisition of Full-Length cDNA 4-1. Design of Primers to be Used for 3' Race PCR Based on the sequence in the nontranslated region on 5' terminal side of luciferase gene obtained by the 5' Race PCR experiment, primers to be used for 3' RACE and those used for Nested PCR were prepared. Synthesis of primers was commissioned to Life Technologies, Japan.

4-2. 3'Race PCR for Acquisition of Full-Length Firefly Luciferase

With use of the firefly full-length cDNA library prepared as described above as a template, 3'-Race PCR was performed by applying the primer prepared from the base sequence of the nontranslated region on 5' terminal side of objective firefly luciferase (Luci5-2-Full-F1, 5'-AGTATTCTTGTGCAGT-GTTTAATTTA-3', SEQ ID NO: 23), GeneRacer3' Primer (5'-GCT GTC AAC GAT ACG CTA CGT AAC G-3'; SEQ ID NO: 24), and Gene Racer3' Nested Primer (5'-CGC TAC GTA ACG GCA TGA CAG TG-3': SEQ ID NO: 25). The used GeneRacer3' Primer and GeneRacer3' Nested Primer were contained in a full-length cDNA synthesis reagent GeneRacer kit (Invitrogen). In order to efficiently amplify luciferase gene by 3'-RACE PCR, the genes once amplified by PCR were used as a template, and the nested PCR which further specifically amplifies the gene was carried out with use of the inside primer pair. The PCR was carried out with use of polymerase Ex-Taq (Takara Bio Inc.) according to the manual.

As the first PCR, a primer pair comprised of a primer prepared from base sequence of the nontranslated region on 5' terminal side and GeneRacer 3' Primer was used to amplify the luciferase gene. To 20 µl of PCR reaction comprising 10× Ex Taq Buffer (20 mM $Mg^{2+}$ plus) diluted tenfold, dNTP Mixture at a final concentration of 0.2 mM (2.5 mL for each base), TaKaRa Ex Taq (5 U/µl) at a final concentration of 0.05 U/µl, and primers at a final concentration of 0.3 µM, added was 0.4 µl of firefly full-length cDNA library solution. Here, the concentration of the firefly full-length cDNA library solution was not determined. In the PCR reaction, the solution was thermally denatured for 2 minutes at 94° C., and then the cycle consisting of 30 seconds at 94° C., 30 seconds at 50° C., and 2 minutes at 72° C. was repeated 30 times, followed by an elongation reaction at 72° C. for 5 minutes. After the PCR reaction, 1 µl of the PCR reaction solution was applied to 1% tris acetic acid buffer (TAE) agarose gel electrophoresis, and observed bands of amplified genes under exposure of ultraviolet after dyeing with ethidium bromide. Slight gene amplification was confirmed, and thus nested PCR was performed with use of the PCR reaction solution as a template.

As the Nested PCR, the luciferase gene was amplified with use of a primer pair consisting of a primer for Nested PCR (Luci5-2-Full-F2, 5'-AGTATTCTTGTGCAGTGTTTAATT-TAAAGAACAA-3', SEQ ID NO: 26) and GeneRacer3' Nested Primer. To 10 µl of PCR reaction solution comprising 10× Ex Tag Buffer (20 mM $Mg^{2+}$ plus) diluted tenfold, dNTP Mixture at a final concentration of 0.2 mM (2.5 mL for each base), TaKaRa Ex Taq (5 U/µl) at a final concentration of 0.05 U/µl, and primers at a final concentration of 0.3 µM, added was 1.0 µl of a solution prepared by diluting the first PCR reaction solution in tenfold with sterilized water, as a template. In the PCR reaction, the solution was thermally denatured for 2 minutes at 94° C., and then the cycle consisting of 30 seconds at 94° C., 30 seconds at 50° C., and 2 minutes at 72° C. was repeated 30 times, followed by an elongation reaction at 72° C. for 5 minutes. After the PCR reaction, 1 μl of PCR reaction solution was applied to 1% tris acetic acid buffer (TAE) agarose gel electrophoresis, and observed bands of amplified genes under exposure of ultraviolet after dyeing with ethidium bromide. It was confirmed that the gene was efficiently amplified at about 2 kbp.

4-3. Determination of Base Sequence of the Gene Amplified by 3'-Race

In order to identify the base sequence amplified by 3'-RACE, PCR product was purified by gel extraction, followed by subcloning and direct sequencing. The details are given below.

With the combination of primers which efficiently amplified the genes at about 2 kbp, PCR (final volume 20 μl) was carried out, and the objective gene fragments were collected by means of gel extraction. The gel extraction was carried out with use of Wizard SV Gel and PCR Clean-Up System (Promega KK) according to the manual. The subcloning of the PCR product extracted from gel was carried out by means of TA cloning. The TA cloning was performed with us of pGEM-T Easy Vector Syetem (Promega KK) according to the manual. Subsequently, the vector DNA was transformed to *E. Coli* (TOP10 strain or DH5α strain), and the insert positive colonies were selected by means of blue-white screening. The selected colonies were subjected to a direct colony PCR, and confirmed that the gene was introduced. In the direct colony PCR, a primer pair consisting of M13-F(-29) Primer(5'-CAC GAC GTT GTA AAA CGA C-3': SEQ ID NO: 21) and M13 Reverse (5'-GGA TAA CAA TTT CAC AGG-3': SEQ ID NO 22) was used. To 10 μl of PCR reaction comprising 10× Ex Tag Buffer (20 mM $Mg^{2+}$ plus) diluted tenfold, dNTP Mixture at a final concentration of 0.2 mM (2.5 mL for each base), TaKaRa Ex Taq (5 U/μl) at a final concentration of 0.05 U/μl, and primers at a final concentration of 0.2 μM, added was a small amount of *E. coli* colony as a template. In the PCR reaction, the solution was thermally denatured for 1 minutes at 94° C., and then the cycle consisting of 30 seconds at 94° C., 30 seconds at 50° C., and 2 minutes at 72° C. was repeated 25 times, followed by an elongation reaction at 72° C. for 2 minutes. After the PCR reaction, 2 μl of the PCR reaction solution was applied to 1% tris acetic acid buffer (TAE) agarose gel electrophoresis, and observed bands of amplified genes under exposure of ultraviolet after dyeing with ethidium bromide.

As for the PCR reaction solutions for which the amplification was confirmed, the base sequence of the gene was determined by a direct sequencing method. With use of a PCR product purification kit ExoSAP-IT (GE Healthcare Bioscience), extra dNTP and primers containing the PCR reaction solution were removed, and prepared a template for PCR direct sequencing. A sequencing reaction solution was prepared with use of BigDye Terminator v3.1 Cycle Sequencing Kit (Applied biosystems), and the sequencing reaction was carried out by a thermal cycler. The primers used for sequencing were a vector primer or a primer specific to a gene. Purification of the PCR products and sequencing were each performed according to the manual. After the sequencing reaction, the purification was performed as follows. To the reaction solution, added was 2.5 times by weight of 100% ethanol, followed by precipitation of the nucleic acid with a centrifuge. After removing the supernatant, the precipitate was washed by adding 70% ethanol and the nucleic acid were precipitated by a centrifuge. After removing the supernatant, the precipitate was dried finally. To the purified precipitate, 15 μl of Hi-Di Formamide (Applied Biosystems) was added and dissolved. The solution was thermally denatured at 94° C. for 2 minutes, cooled on ice, and used as a sample for determination of base sequence. With respect to the sample, the base sequence was determined with use of Applied Biosystems 3130x1 genetic analyzer (Applied Biosystems). The analytical method of the base sequence was carried out according to the manual.

A full-length firefly luciferase gene was obtained by sequencing. As for the base sequence (SEQ ID NO: 2) or the sequence translated into the amino acid (SEQ ID NO: 1), the homology search was performed by utilizing the blastx or blastp search provided by NCBI. In each search, it was confirmed that the base sequence has high homology with the base sequences of known firefly luciferases. The base sequence obtained in the experiments and analysis described above was determined as a full-length cDNA sequence of a novel firefly luciferase.

Hereinafter, the novel luciferase is referred to as SP1 luciferase.

EXAMPLE 2

Determination of Enzymatic Parameters of Novel Luciferase

1. Protein Expression of Novel Firefly Luciferase Gene

For expressing firefly luciferase gene in *E. coli*, it was introduced into a pRSET-B vector (Invitrogen). According to the standard method, the gene expression vector was constructed by experiments described below.

1-1. Modification of Recognition Site of Restriction Enzyme of Novel Firefly Luciferase Gene According to the base sequence determined as described above, the novel luciferase gene contains the recognition sequence of restriction enzymes BamHI and EcoRI. The genetic modification was carried out so that the amino acid sequence of luciferase was maintained and the recognition sequences in these base sequences were removed. This treatment was carried out for the purpose of facilitating the introduction of luciferase gene into an expression vector which is explained below. The introduction of genetic mutation was carried out by following the method described in "a experimental method of gene functional inhibition-from simple and secure gene function analysis to application to gene therapy" edited by Kazunari Taira, Yodosha, published in 2001, pages 17-25). The base sequence after mutation introduction is represented by SEQ ID NO: 3.

1-2. Introduction of Novel Firefly Luciferase into Expression Vector

In order to introduce luciferase gene to a region between BamHI site and EcoRI site of pRSET-B vector, a primer comprising intiation codon and recognition sequence of restriction enzyme BamHI GGATCC therebefore, and a primer comprising termination codon and recognition sequence of restriction enzyme EcoRI GAATTC thereafter were prepared. With use of the primer pair, a fragment containing the aforementioned restriction enzyme recognition sites on both terminals of luciferase gene was amplified. The PCR was carried out with use of polymerase KOD-Plus (Toyobo Co., Ltd.) according to the manual.

To 10 μl of PCR reaction comprising 10× PCR Buffer diluted ten fold, dNTP Mixture at a final concentration of 0.2 mM (2.5 mL for each base), $MgSO_4$ at a final concentration of 1.0 mM, Toyobo KOD-Plus (1 U/μl) at a final concentration of 0.02 U/μl, and a primer pair at a final concentration of 0.3 μM, added was 0.4 μl of luciferase gene not containing BamHI and EcoRI recognition sequences as a template. In the PCR reaction, the solution was thermally denatured for 2 minutes at 94° C., and then the cycle consisting of 30 seconds at 94° C., 30 seconds at 55° C., and 2 minutes at 68° C. was repeated 30 times, followed by elongation reaction at 68° C. for 5 minutes. After the PCR reaction, 1 µl of PCR reaction solution was applied to 1% tris acetic acid buffer (TAE) agarose gel electrophoresis, and observed bands of amplified genes under exposure of ultraviolet after dyeing with ethidium bromide. The gene amplification was confirmed, and thus this PCR reaction solution was precipitated and concentrated by an ethanol precipitation method, dissolved by adding 4 µl of 10× H Buffer for restriction enzyme treatment, restriction enzymes BamHI (Toyobo Co., Ltd.) and EcoRI (Toyobo Co., Ltd.) of 2 µl each, and 32 µl of sterile deionized ion water, and treated with the restriction enzymes after maintaining the temperature at 37° C. for 2 hours. Subsequently, the reaction solution was precipitated and concentrated by an ethanol precipitation method, and dissolved in sterile deionized ion water. The solution was applied to 1% TAE agarose gel electrophoresis, followed by dyeing with ethidium bromide. The gel containing DNA bands which were confirmed under exposure of ultraviolet were clipped out with a knife. From the clipped gel, DNA was extracted with use of Wizard(R) SV Gel and PCR Clean-UP System (Promega KK). These operations were performed according to the manual. Subsequently, with use of Ligation Pack (Nippon Gene) in accordance with the manual, the extracted DNA was introduced into pRSET-B vector which was treated by BamHI and EcoRI in advance by a similar method. This vector DNA was transformed to $E.$ $coli$ JM109 (DE3) strain and allowed colony formation.

Direct colony PCR was carried out using the obtained colony as a template, and the luciferase gene introduced into pRSET-B was amplified. The direct colony PCR was performed with use of a primer pair of T7 promoter Primer (5'-TAA TAC GAC TCA CTA TAG GG-3': SEQ ID NO: 27) and T7 Reverse Primer (5'-CTA GTT ATT GCT CAG CGG TGG-3': SEQ ID NO: 28). To 10 µl of PCR reaction comprising 10× Ex Taq Buffer (20 mM $Mg^{2+}$ plus) diluted tenfold, dNTP Mixture at a final concentration of 0.2 mM (2.5 mL for each base), TaKaRa Ex Taq (5 U/µl) at a final concentration of 0.05 U/µl, and primers at a final concentration of 0.2 µM, added was a small amount of $E.$ $coli$ colony as a template. In the PCR reaction, the solution was thermally denatured for 2 minutes at 94° C., and then the cycle consisting of 30 seconds at 94° C., 30 seconds at 50° C., and 2 minutes at 72° C. was repeated 25 times, followed by an elongation reaction at 72° C. for 5 minutes. After the PCR reaction, 1 µl of PCR reaction solution was applied to 1% tris acetic acid buffer (TAE) agarose gel electrophoresis, and observed bands of amplified genes under exposure of ultraviolet after dyeing with ethidium bromide.

As for the PCR reaction solution for which amplification was confirmed, the base sequence of the gene was determined by a direct sequencing method. With use of PCR product purification kit ExoSAP-IT, the extra dNTP and primers were removed thereby preparing a template for PCR direct sequencing. The sequencing reaction solution containing the template was prepared by using BigDye Terminator v3.1 Cycle Sequencing Kit, and sequencing reaction was carried out with use of a thermal cycler. A vector primer or a primer specific to the gene was used for sequencing. Purification and sequencing were carried out according to the manual. After sequencing reaction, the reaction product was purified as explained below. 2.5 times by weight of 100% ethanol was added to the reaction solution, and the nucleic acid was precipitated by a centrifuge. After removing the supernatant, the precipitate was washed by adding 70% ethanol and the nucleic acid was precipitated by a centrifuge. After removing the supernatant, the precipitation was finally dried. The purified precipitate was dissolved by adding 15 µl of Hi-Di Formamide (Applied Biosystems). The solution was thermally denatured for 2 minutes at 94° C., cooled on ice, and used as a sample for determination of the base sequence. With respect to the sample, the base sequence was determined by Applied Biosystems 3130x1 Genetic Analyzer, and confirmed that the gene was introduced into a gene expression vector pRSET-B.

2. Purification of a Luminescent Protein 0.5 µl of luciferase vector was added to 50 µl of the $E.$ $coli$ solution containing JM109 (DE3), and the solution was incubated on ice for 10 minutes, then at 42° C. for 1 minute, and incubated on ice for 2 minutes. Subsequently, 50 µl of the $E.$ $coli$ solution was added to 200 µl of SOC culture medium, and incubated during shaking for 20 minutes at 37° C. 100 µl of the incubated sample was streaked to LB culture medium plate (containing 100 µg/ml of Ampicillin) and incubated at 37° C. overnight. On the next day, the obtained colony was incubated in LB culture medium of 500 ml scale at 37° C. for 24 hours and at 18° C. for 24 hours. After the incubation of 48 hours, the fungus body was collected by a centrifuge, resuspended in 0.1 M Tris-HCl solution (pH 8.0), and subjected to be ultrasonic fragmentation. The fragmented solution of the fungus body was subjected to centrifuge separation (15,000 rpm, 10 minutes), and the supernatant was collected by removing the precipitate. To the column having 2 ml of a bed volume, 500 µl of Ni-Agar suspension solution and 2 ml of 0.1 M Tris-HCl were added to equilibrate the column. The collected supernatant was added to the column, and let it pass through the column. While all the supernatant was passed through the column, the operations were all carried out at 4° C. The column was washed with 2 ml of 25 mM imidazole/0.1 M Tris-HCl solution. To the washed column, 2 ml of 500 mM imidazole/0.1 M Tris-Hcl solution was added to elute luciferase. The eluted sample was filtrated with gel filtration column PD-10 (GE Healthcare) and demineralized. The demineralized sample was subjected to ultrafiltration with Vivaspin6 (Sartorius K.K.), and glycerin was added to the concentrated sample to prepare 50% glycerine solution. The solution was preserved at −20° C.

3. Measurement of Luminescence Spectra

With use of LumiFlSpectroCapture (ATTO) as an apparatus for measurement, to a solution of 0.1 M citric acid/0.1 M $Na_2HPO_4$ buffer (pH 6.0-8.0) containing 1 mM D-luciferin, 2 mM of ATP and 4 mM $MgCl_2$, the purified enzyme was added at a final concentration of 1 to 10 µg/ml, and after 15 seconds of addition of the enzyme luminescence spectra was measured. The measurement results were shown in FIG. 1.

FIG. 1 shows that the maximum luminescent wavelength and intensity of the obtained luciferase greatly varied depending on pH. The luciferase has maximum luminescent wavelength at approximately 580 nm at pH 8. As the pH decreases, the maximum luminescent wavelength becomes gradually increased, and it was approximately 587 nm at pH 7.5, 598 nm at pH 7.0, 606 nm at pH 6.5, and 609 nm at pH 6.0. The maximum luminescent intensity was confirmed at pH 7.5.

4. Kinetic Analysis 4-1. Determination of Concentrations of D-Luciferin and ATP

A concentration of D-luciferin in a D-luciferin solution and that of ATP in an ATP solution were determined as described below.

With use of UV-Visible Spectrometer (Hitachi), ultraviolet visible absorption spectra were measured for the D-luciferin solution and ATP solution. Based on the measurement results and $\epsilon$ values indicated below, each concentration was calculated.

D-luciferin: λmax 328 nm, $\epsilon$ 18200, pH 5.0
ATP: λmax 259 nm, $\epsilon$ 15400, pH 7.0

The measurements were carried out ten times for each sample, and the average of absorbency was used for the calculation. The Km value was calculated as is described below by using the D-luciferin solution and ATP solution whose concentrations were determined.

4-2. Measurement of Km for D-Luciferin

Under various concentrations of D-luciferin, the luminescent intensity was measured for the obtained luciferase. Based on the measurement results, Km values with respect to D-luciferin were calculated.

Twelve types of D-luciferin of various concentrations were prepared by adding D-luciferin to 0.1 M Tris-HCl (pH 8.0). These solutions contain D-luciferin at final concentrations of 0.625, 1.25, 2.5, 5, 10, 20, 40, 80, 160, 320, 480, and 640 μM. These D-luciferin solutions were each injected into 96-hole microplate at an amount of 50 μl. A solution of 0.1 M Tris-HCl (pH 8.0) containing each of the purified luciferase, 4 mM of ATP, and 8 mM of $MgSO_4$ was connected to the standard pump of the luminometer, and the measurements was carried out at the same time as addition of 50 μl of the solution to the well. A Luminescensor (ATTO) was used for the measurements. Measurements were repeated 3 times for each luciferin concentration.

The peak intensity of the obtained photo count value was plotted with respect to luciferin concentration S, defining the initial rate as V. The plots were subjected to curve fitting of Michaelis Menten type, thereby giving Km values. The curve fitting was performed by a nonlinear least-squares method, and the search of the parameter was performed by a Newton method.

4-3. Measurement of Km Value with Respect to ATP

Under various ATP concentrations, the luminescent intensity of the obtained luciferase was measured. Based on the results, Km values with respect to ATP was determined.

Various 12 types of ATP solutions were prepared by adding ATP to 0.1 M Tris-HCl (pH 8.0). These solutions contain ATP at final concentration of 5, 10, 20, 40, 80, 160, 320, 480, 640, 800, 1280, 1600, or 1920 μM. These ATP solutions were each injected into 96-hole in a microplate at a volume of 50 μl. 0.1 M Tris-HCl (pH 8.0) solution containing each purified luciferase, 1 mM D-luciferin, and 8 mM $MgSO_4$ was connected to a standard pump of a luminometer, and the measurement was carried out at the same time as addition of 50 μl of the solution to wells. Measurement was repeated 3 times for each ATP concentration.

The peak intensities of the obtained photon count value were plotted with respect to ATP concentration S, with an initial rate V. The plots were subjected to curve fitting of Michaelis Menten type, thereby giving Km value. The curve fitting was performed by a nonlinear least-squares method, and the search of the parameter was performed by a Newton method.

Km values with respect to D-luciferin and Km values with respect to ATP which were determined as described above were shown in Table 1. Table 1 also indicates Km values for known firefly luciferases, measured in a similar manner. GL3 is a luciferase derived from a known firefly. Further, ELuc, CBG, and CBR are luciferases derived from known click beetles. These known were commercially available.

TABLE 1

| Comparison of Km value | | |
|---|---|---|
| | Km | |
| | D-luciferin (uM) | ATP (uM) |
| SP1 | 44.6 | 195 |
| GL3 | 15.7 | 71.3 |
| ELuc | 12.7 | 182 |
| CBG | 1.44 | 58.4 |
| CBR | 33.3 | 47.1 |

Further, FIG. 2 indicates these Km values as plots with respect to D-luciferin concentration and ATP concentration. This figure shows that SP1 luciferase has higher Km values with respect to ATP and D-luciferin than those of known luciferase.

EXAMPLE 3

Measurement of Luminescent Intensity

The luminescent intensity of SP1 luciferase was compared with those of known luciferases and Rhodamine 6G.

1. Measurement of Chemical Luminescence by Rhodamine 6G

Rhodamine 6G was dissolved into 0.1 M citric acid/0.2 M $Na_2HPO_4$ (pH 4.0) solution. The Rhodamine 6G solution was centrifuged for 1 minute at 15,000 rpm, and the supernatant was collected. The collected supernatant is diluted with 0.1 M citric acid/0.2 M $Na_2HPO_4$ solution 1000 fold, and the absorbance thereof was measured. Measurement was carried out by NanoVue (GE Healthcare). The measurement at 530 nm was repeated 5 times, and the average absorbance 0.048 was obtained. The concentration of the original Rhodamine 6G solution was calculated by using $\epsilon$ value of Rhodamine (1.16× $10^5$ $mol^{-1}cm^{-1}$), and the value 414 μM was obtained. The solution was diluted with 0.1 M citric acid/0.2 M $Na_2HPO_4$ solution (pH 4.0) to prepare 30 μM of a diluted solution.

Solution 1 having the following composition was prepared with use of the diluted solution.

TABLE 2

| Composition of Solution 1 | | |
|---|---|---|
| 0.1M citrate/0.2M $Na_2HPO_4$ (pH 4.0) | 989 μl | |
| Rhodamine 6G solution (30 μM) | 1 μl | (Final concentration 30 nM) |
| 30% hydrogen peroxide solution | 10 μl | (Final concentration 0.3%) |
| Solution 1 | 1000 μl | |

Solution 2 was prepared by dissolving bis (2,4,6-trichlorophenyl)oxlate (TCPO) so that the final concentration thereof is 3 mM.

100 μl of solution 1 was injected for each well of 96-hole microplate. Measurement was started at the same time as addition of 50 μl of solution 2 with use of a pump, and integration value of photon counts for 10 seconds from addition of solution 2 was obtained. Measurement was carried out with a Luminescensor (ATTO), and light of from 300 nm to 650 nm was obtained. The measurement was repeated 10 times.

2. Measurement of Chemical Luminescence by P. pyralis Luciferase and SP1 Luciferase To 50 μl of a solution containing JM109 (DE3) strain, added was 0.5 μl of a solution containing luciferase expression vectors. The solution was cooled on ice for 10 minutes, maintained at 42° C. for 1 minute, and incubated on ice for 2 minutes. Subsequently, 50 μl of the E. coli solution was added to 200 μl of the SOC culture medium. The mixed solution of E. coli/SOC culture medium was incubated at 37° C. during shaking for 20 minutes. 100 μl of the incubated sample was streaked on LB culture medium plate (containing 100 μg/ml of Ampicillin), and incubated at 37° C. over night. On the next day, the generated colonies were picked up, and cultivated in 500 ml scale of LB culture medium. The cultivation was performed at 37° C. for 24 hours and at 18° C. for 24 hours. After the cultivation of 48 hours, the fungus body was collected by centrifuge, and resuspended in 0.1 M Tris-HCl (pH 8.0), followed by ultrasonic fragmentation. The fragmented fungus body solution was centrifuged (15,000 rpm, for 10 minutes), and the supernatant was collected by removing the precipitate. A column having a bed volume of 2 ml was equilibrated with 500 μl of Ni-Agar suspended solution and 2 ml of 0.1 M Tris-HCl solution. The collected supernatant was added to the column, and let it pass through the column. Until all the supernatant passed through the column, the operations was all carried out at 4° C. The column was washed with 2 ml of 25 mM imidasol/0.1 M Tris-HCl solution. To the washed column, 2 ml of 500 mM imidasol/0.1 M Tris-HCl solution was added to elute luciferase. The eluted sample was filtrated with gel filtration column PD-10 (GE Healthcare) and demineralized. The demineralized sample was subjected to ultrafiltration with Vivaspin 6 (Sartorius K.K.).

A concentration of the obtained sample was measured by a colorimetric method, and the concentrations of P. pyralsis luciferase and SP1 luciferase were confirmed. The aforementioned luciferase was diluted into 0.1 M citric acid/0.2 M $Na_2HPO_4$ (pH 8.0) so that the final concentration thereof is 1 μg/ml.

50 μl of luciferase solution was injected into 96-hole microplate. 50 μl of a solution containing 2 mM D-luciferin, 4 mM ATP, and 8 mM $MgSO_4$/0.1 M Tris-HCl (pH 8.0) was added by a standard pump of luminometer, and measurement was carried out at the same time as the addition. For 10 seconds from addition of the solution, the integration values of Photon counts were obtained. Measurement was carried out using a Luminescensor (ATTO) and light of from 300 nm to 650 nm was obtained. Each of the measurements was repeated 6 times.

3. Measurement Results

Intensities of chemical luminescence of Rhodamine 6G, P. pyralus luciferase, and SP1 luciferase are shown in FIG. 3.

From FIG. 3, SP1 luciferase was proved to indicate 23.3 times of luminescent intensity of that of Rhodamine 6G. SP1 luciferase was proved to indicate 4.9 times of luminescent intensity in comparison to that of P pyralis.

EXAMPLE 4

Expression of SP1 Luciferase in a Mammal Cell

SP1 luciferase was expressed in a HeLa cell, and the luminescent intensity in a cell was measured.

For introduction of SP1 luciferase gene, four types of expression vectors were prepared. Nucleic acids each containing a gene prepared by deleting recognition sequences of BamHI and EcoRI from the original SP1 luciferase gene obtained from Luciola sp1 (SEQ ID NO: 3), a gene further optimized for expression in a mammal cell (SEQ ID NO: 4), and two types of genes to which Kozak sequence was further added (SEQ ID NOS: 29 and 30) were each inserted into the multi-cloning site between BamHI and EcoRI of pcDNA3.1 (+) vector (Invitrogen). Further, for comparison, a nucleic acid containing a known P. pyralis luciferase gene optimized for expression in a mammal cell was inserted into pcDNA3.1 (+) vector similarly.

Figure 4:
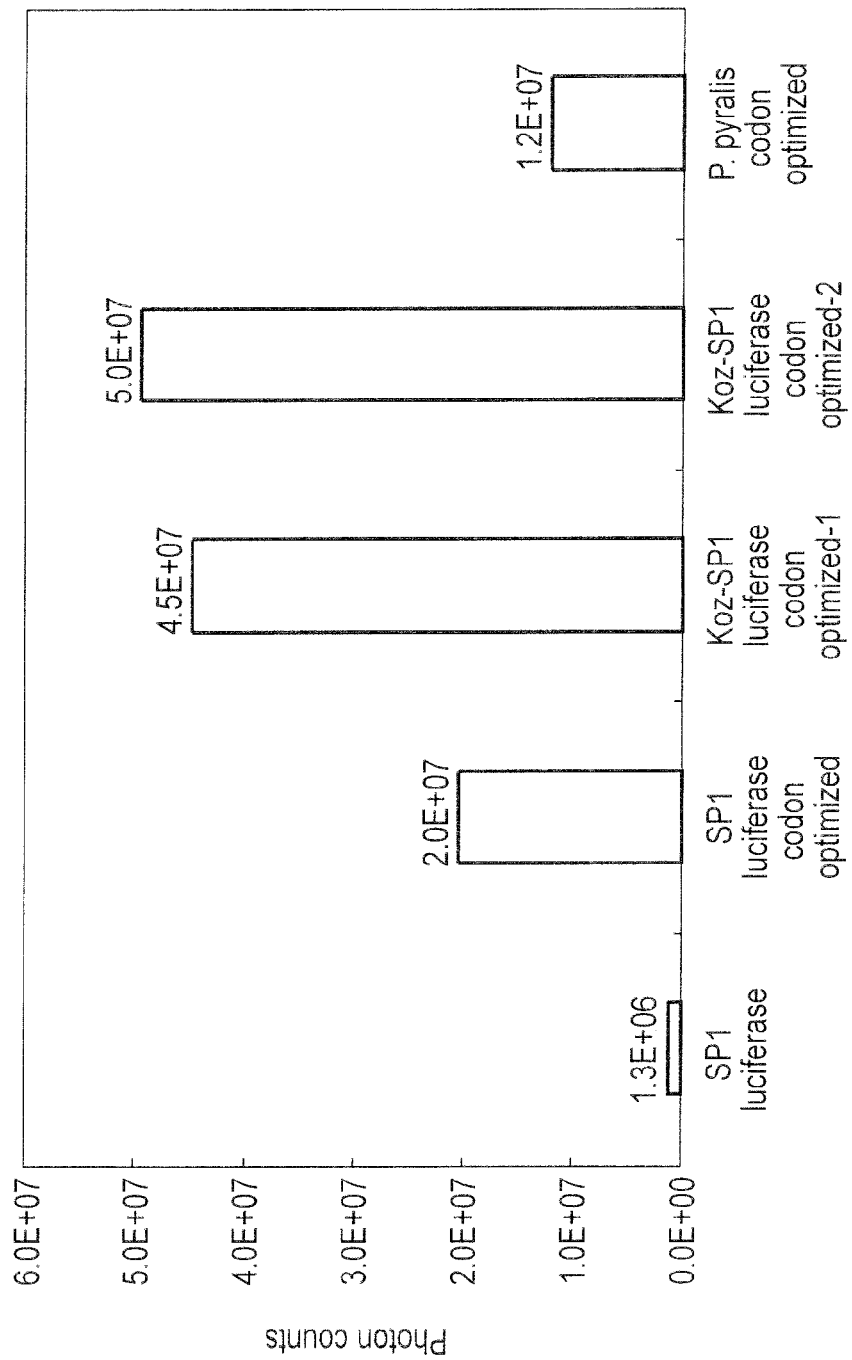
FIG. 4 compares SP1 luciferase and *P. pyralis* luciferase expressed in a mammal cell with respect to luminescent intensity.

Five types of plasmids obtained in such a manner described above were each subjected to gene transfection to a HeLa cell by a lipofection method, and D-MEM culture medium was exchanged after 24 hours. Right before the measurement, D-luciferin was added at a final concentration of 1 mM, and the luminescent intensity was measured with use of Kronos (ATTO). The results are shown in FIG. 4. The luminescent intensities shown in FIG. 4 are integration values for 10 seconds.

According to FIG. 4, optimization of codons of SP1 luciferase increased the luminescent intensity 16.2 times upon expression in a HeLa cell. Further, addition of Kozak sequence increased the intensity 34.6 times for Koz-SP1 luciferase codon optimized-1 and 38.5 times for Koz-SP1 luciferase codon optimized-2 in comparison to SP1 luciferase without codon optimization.

Furthermore, SP1 luciferase, Kozak-SP1 luciferase-1, and Kozak-SP2 luciferase-2 after codon optimization each indicated 1.7 times, 3.7 times, and 4.1 times of luminescent intensity, respectively, in comparison to that of P. pyralis luciferase after codon optimization.

EXAMPLE 5

Change in Luminescence Intensity Upon Introduction of Mutations to SP1 Luciferase 1. Preparation of Mutants SP1 luciferase was prepared by introducing mutations to the amino acid sequence thereof.

The introduced mutations were substitution of aspartic acid at position 438 by glycine (D438G), substitution of isoleucine at position 532 by arginine (I532R), substitution of glutamic acid at position 356 by arginine (E356R), and substitution of valine at position 368 by alanine (V368A) in SEQ ID NO:1, and each of these four mutations were each introduced solely or any combination thereof were introduced into the original SP1 luciferase.

Mutations were introduced according to the methods described in Asako Sawano and Atsushi Miyawaki, Nucleic Acids Research, 2000, Vol. 28, No. 16. The primer used were those represented by SEQ ID NO: 31 (for D438G), SEQ ID NO: 32 (for 532R), SEQ ID NO: 33 (for E356R), and SEQ ID NO: 34 (for V368A). After introduction of mutations, sequencing was performed to confirm that the object genes were introduced.

Among the prepared mutants, those to which mutations D438G, I532R, and E356R were introduced is referred to as "SP1 mutant 1," and those to which mutations E356R and V368A were introduced is referred to as "SP1 mutation 2." The base sequence and amino acid sequence of SP1 mutant 1 are represented by SEQ ID NO: 35 and SEQ ID NO: 37, respectively. The base sequence and amino acid sequence of SP1 mutant 2 are represented by SEQ ID NO: 36 and SEQ ID NO: 38, respectively.

2. Study on Luminescence Activity of Mutants

With respect to the SP1 mutant 1 and SP1 mutant 2, the luminescence activity was examined.

The fragment of the nucleic acid having the base sequence of SEQ ID NO: 35 was inserted into between SgfI site and PmeI site of a pF9A CMV hRluc-neo FlexiR vector (Promega). The fragment of the nucleic acid having the base sequence of SEQ ID NO: 36 was inserted into between SgfI site and PmeI site of another pF9A CMV hRluc-neo FlexiR vector. Two types of the obtained expression vectors were each introduced into HeLa cells, and mutants were expressed.

The luminescence intensity of two types of cells expressing mutants was detected by using a cell expressing the original SP1 luciferase without mutations as a comparison. Here, the luminescence intensity of each Hela cell was corrected using the luminescence based on hRluc gene of pF9A CMV hRluc-neo FlexiR vector (Promega) as an internal standard.

FIG. 5 shows luminescence intensity of the original SP1 luciferase and each mutants from immediately after addition of D-luciferin to 120 minutes after the addition. FIG. 6 shows temporal change of the luminescence intensity of hRluc luciferase used as an internal standard from immediately after addition of Coelenterazine to 120 minutes after the addition.

Figure 7:
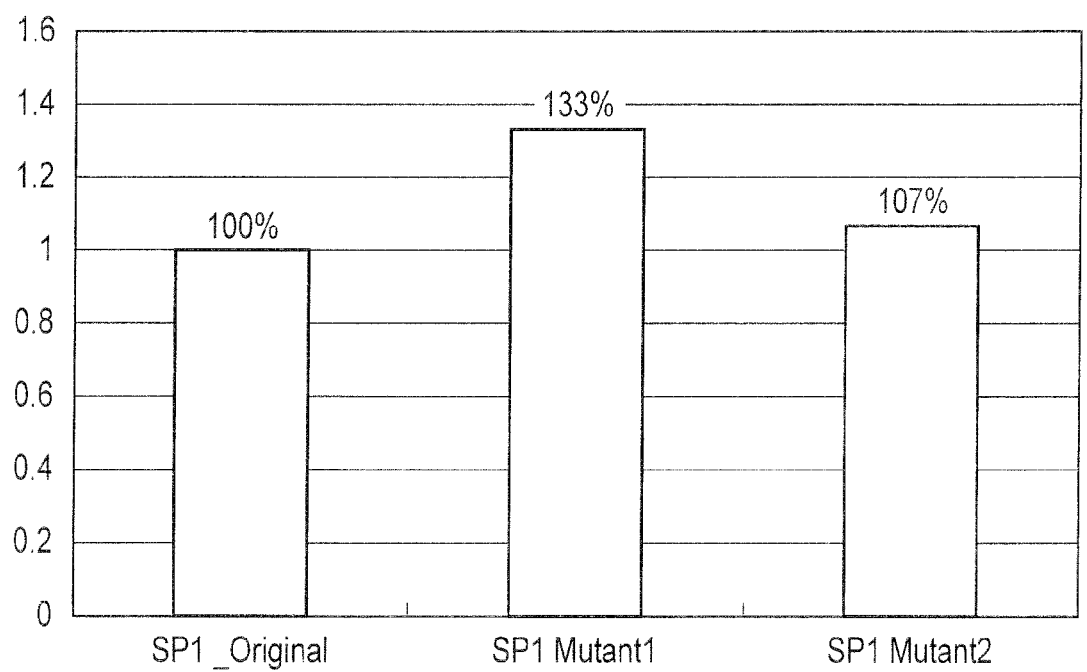
FIG. 7 compares luminescence intensity between the original SP1 luciferase and two types of mutants at the time point of identification.

FIG. 7 shows the ratio of each luminescence intensity of 90 minutes after the addition which was corrected by hRluc luminescence of 10 minutes after the addition.

As is shown by FIG. 7, the luminescence intensity was increased in mutant 1 and mutant 2 in comparison to the original SP1.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A luciferase comprising an amino acid sequence represented by SEQ ID NO: 1.

2. The luciferase according to claim 1, wherein the amino acid sequence comprises at least one substitution of a group consisting of:
- D438G substitution in which an amino acid corresponding to an aspargic acid at position 438 of the amino acid sequence of SEQ ID NO: 1 is glycine;
- I532R substitution in which an amino acid corresponding to an isoleucine at position 532 of the amino acid sequence of SEQ ID NO: 1 is arginine;
- E356R substitution in which an amino acid corresponding to a glutamic acid at position 356 of the amino acid sequence of SEQ ID NO: 1 is arginine; and
- V368A substitution in which an amino acid corresponding to a valine at position 368 of the amino acid sequence of SEQ ID NO: 1 is alanine.

3. The luciferase according to claim 1, wherein an amino acid corresponding to an aspargic acid at position 438 of the amino acid sequence of SEQ ID NO: 1 is glycine,
an amino acid corresponding to an isoleucine at position 532 of the amino acid
an amino acid corresponding to a glutamic acid at position 356 of the amino acid sequence of SEQ ID NO: 1 is arginine.

4. The luciferase according to claim 1, wherein an amino acid corresponding to a glutamic acid at position 356 of the amino acid sequence of SEQ ID NO: 1 is arginine, and
an amino acid correspoding to a valine at position 368 of the amino acid sequence of SEQ ID NO: 1 is alanine.

* * * * *